United States Patent
Izumi et al.

(10) Patent No.: US 7,427,270 B2
(45) Date of Patent: Sep. 23, 2008

(54) SLEEP STAGE DETERMINATION APPARATUS

(75) Inventors: Shuichi Izumi, Asaka (JP); Toshiaki Sasaki, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/393,668

(22) Filed: Mar. 31, 2006

(65) Prior Publication Data

US 2006/0169282 A1    Aug. 3, 2006

(51) Int. Cl.
    *A61B 5/08*    (2006.01)
    *A61B 5/103*   (2006.01)
    *A61B 5/117*   (2006.01)

(52) U.S. Cl. ............... 600/534; 600/529; 600/595

(58) Field of Classification Search ......... 600/529–543, 600/300, 301, 595
See application file for complete search history.

(56) References Cited

U.S. PATENT DOCUMENTS

| | | | | |
|---|---|---|---|---|
| 4,320,766 A | * | 3/1982 | Alihanka et al. ............ 600/484 |
| 5,515,865 A | * | 5/1996 | Scanlon ...................... 600/534 |
| 5,684,460 A | * | 11/1997 | Scanlon ................... 340/573.1 |
| 6,454,724 B1 | * | 9/2002 | Greene ........................ 600/534 |
| 6,811,538 B2 | * | 11/2004 | Westbrook et al. .......... 600/529 |
| 7,150,718 B2 | * | 12/2006 | Okada et al. ................. 600/538 |
| 2004/0210155 A1 | * | 10/2004 | Takemura et al. ............ 600/534 |
| 2006/0162074 A1 | * | 7/2006 | Bader ............................ 5/421 |

FOREIGN PATENT DOCUMENTS

JP     2002-219116     8/2002

* cited by examiner

*Primary Examiner*—Charles A. Marmor, II
*Assistant Examiner*—Navin Natnithithadha
(74) *Attorney, Agent, or Firm*—McDermott Will & Emery LLP

(57) ABSTRACT

Disclosed is a sleep stage determination apparatus which comprises respiratory-signal detection means for detecting a variation of a respiratory signal from the body of a human subject, and sleep-stage determination means for determining a plurality of sleep stages using only the respiratory-signal variation. The sleep stage determination apparatus of the present invention can eliminate the need for detecting a plurality of biological signals and have simplified sensor and circuit configurations designed to detect only the respiratory signal variation which is relatively easily detectable. This makes it possible to reduce a detection error and achieve enhanced determination accuracy or creditability.

9 Claims, 16 Drawing Sheets

SLEEP STAGE DETERMINATION APPARATUS

TECHNICAL FIELD

The present invention relates to an apparatus for determining a plurality of sleep stages.

BACKGROUND ART

Heretofore, particularly in medical wards, a determination of a plurality of sleep stages has been made based on a polysomnographic technique designed to acquire data about electroencephalogram electrooculogram and sub-mental electromyogram, and discriminate the sleep stages based on the acquired data. Unfortunately, this technique is unsuitable for general households, because the measurement for acquiring the data involves a troublesome preparatory step of attaching a plurality of electrodes onto the body of a human subject, and requires expertise in handling measuring devices.

Form this standpoint, an apparatus has been disclosed that is designed to detect at least one of a gross body movement and a heart rate of a human subject on bedclothes using a vibration sensor, such as a piezoelectric element, disposed under bedclothes designed, and calculate an occurrence number of gross body movements or a heart-rate variation based on the detected data, so as to discriminate a plurality of sleep stages based on a correlation between the calculated data and a sleep cycle (see, for example, the following Patent Publication 1).

[Parent Publication 1] Japanese Patent Laid-Open Publication No. 2002-219116

DISCLOSURE OF THE INVENTION

In the apparatus disclosed in the Patent Publication 1, if it is attempted to discriminate the sleep stages based on only an occurrence number of gross body movements, it is hardly said that the sleep stages can be discriminated with high credibility even though a sleep cycle can be roughly detected.

Differently, if it is attempted to discriminate the sleep stages based on only a variation in heart rate, a body movement occurring during a process of detecting heart-rate data from an output of the vibration sensor causes a problem about detection of a low-creditable heart rate due to the heart rate which is originally a weak micro-signal susceptible to body movements.

As measures against the deterioration in detection accuracy of heart rate, the apparatus disclosed in the Patent Publication 1 has to be designed to additionally detect gross body movements, and correct heart-rate data in a manner allowing a heart rate detected during occurrence of a gross body movement to be removed from the heart-rate data so as to prevent such a low-creditable heart rate from being used in calculation of a heart-rate variation. That is, the apparatus disclosed in the Patent Publication 1 is required to detect two types or more of signals.

In view of the above problems, it is an object of the present invention to provide a sleep stage determination apparatus capable of discriminate a plurality of sleep stages with high creditability, using only a respiratory signal from the body of a human subject.

In order to achieve this object, according to a first aspect of the present invention, there is provided a sleep stage determination apparatus comprising respiratory-signal detection means for detecting a variation of a respiratory signal from the body of a human subject, and sleep-stage determination means for determining a plurality of sleep stages using only the respiratory-signal variation.

In the sleep stage determination apparatus set forth in the first aspect of the present invention, the sleep-stage determination means may be operable to discriminate the sleep stages with respect to each of a plurality of unit zones defined by segmenting the respiratory-signal variation on a given time period basis.

Further, the sleep-stage determination means may be operable to discriminate the sleep stages in four classifications consisting of a wake stage, a deep sleep stage, a light sleep stage and a REM sleep stage.

According to a second aspect of the present invention, there is provided a sleep stage determination apparatus comprising respiratory-signal detection means for detecting a variation in a respiratory signal from the body of a human subject, and sleep-stage determination means for determining a plurality of sleep stages using only the respiratory-signal variation. In this sleep stage determination apparatus, the sleep-stage determination means includes: in-bed/out-of-bed determination means for determining between an in-bed state and an out-of bed state, based on the respiratory-signal variation; body-movement determination means for determining the presence and level of a body movement, based on the respiratory-signal variation; wake determination means and intervening-wake determination means for determining between a wake state and a sleep state, based on a determination result of the body-movement determination means; sleep-initiation determination means for determining a sleep-initiation state having a transition from the wake state to the sleep state, based on the respiratory-signal variation, and the respective determination results of the in-bed/out-of-bed and wake determination means; sleep determination means for determining a depth of sleep based on the respiratory-signal variation, and respective determination results of the in-bed/out-of-bed, body-movement, sleep-initiation and wake determination means; and wake-up determination means for determining a wake-up state based on the respiratory-signal variation, and respective determination results of the in-bed/out-of-bed, body-movement, sleep-initiation, wake and sleep determination means.

In the sleep stage determination apparatus set forth in the second aspect of the present invention, the in-bed/out-of-bed determination means may be operable, when the respiratory signal continues for a given time period or more at an amplitude equal to or greater than a given threshold value, to discriminate the in-bed state.

The body-movement determination means may be operable to discriminate one of a gross body movement state, a fine body movement state and a no body movement state, based on a plurality of threshold values assigned, respectively, to an amplitude fluctuation and amplitude level of the respiratory signal and a cycle of the respiratory signal. The term "no body movement state" means a state when a respiratory signal waveform is stable.

The wake determination means may be operable to discriminate one of a wake state, an unsteady state and a steady state, based on a variation of the body movement state within a given time period.

The intervening-wake determination means may be operable, when the body movement continues for a given time period or more at a given level or more, to discriminate the given time period of wake state.

The sleep-initiation determination means may be operable to discriminate the wake state based on a transition pattern of an initial wake state and a variation pattern of the respiratory signal in a region around sleep initiation of the subject, to determine the sleep initiation state.

The sleep-initiation determination means may include deep-sleep determination means for determining a deep sleep state, and REM-sleep/light-sleep determination means for determining a REM-sleep state and a light-sleep state.

Further, the deep-sleep determination means may be operable, when each of a respiratory rate within a given time period, a fluctuation of the respiratory rate and a fluctuation of a respiratory cycle is equal to or less than a given threshold, and there is no body movement within a given time period, to discriminate the deep sleep state.

The REM-sleep/light-sleep determination means may be operable to make a determination based on comparing between a respiratory rate within a given time period and an average respiratory rate of the entire sleep states and counting a successive number of the given time periods, and a determination based on whether an apneic state is present or absent within the given time period, so as to discriminate the REM-sleep state and said light-sleep state in accordance with the determination results.

In the sleep stage determination apparatus set forth in the second aspect of the present invention, the wake-up determination means may be operable, when no wake state appears before a given time period elapses from a time of the last determination of the wake state, to discriminate that the wake-up state occurs at the time of the last determination of the wake state.

The sleep stage determination apparatus set forth in the first or second aspect of the present invention may further include heartbeat signal detection means for detecting a heartbeat-related parameter, and correction means for correcting the sleep stages using the detected heartbeat-related parameter.

As above, the sleep stage determination apparatus set forth in the first or second aspect of the present invention comprises the respiratory-signal detection means for detecting a variation of a respiratory signal from the body of a human subject, and the sleep-stage determination means for determining a plurality of sleep stages using only the respiratory-signal variation. Thus, the sleep stage determination apparatus can eliminate the need for detecting a plurality of biological signals and have simplified sensor and circuit configurations designed to detect only the respiratory signal variation which is relatively easily detectable. This makes it possible to discriminate the plurality of sleep stages while reducing a detection error so as to achieve enhanced determination accuracy or creditability.

In the sleep stage determination apparatus set forth in the first aspect of the present invention, the sleep-stage determination means may be operable to discriminate the sleep stages with respect to each of a plurality of unit zones defined by segmenting the respiratory-signal variation on a given time period basis. Thus, the sleep stages to be discriminated in the in-bed state, the wake state or the sleep state can be clearly classified.

Further, the sleep-stage determination means may be operable to discriminate the sleep stages in four classifications consisting of a wake stage, a deep sleep stage, a light sleep stage and a REM sleep stage. This makes it possible to present the sleep stages to the subject in an easy-to-understand way so as to serve as a means to allow the subject to recognize and manage the quality of sleep by herself/himself.

The sleep stage determination apparatus set forth in the second aspect of the present invention comprises the respiratory-signal detection means for detecting a variation in a respiratory signal from the body of a human subject, and the sleep-stage determination means for determining a plurality of sleep stages using only the respiratory-signal variation. Further, the sleep-stage determination means includes: the in-bed/out-of-bed determination means for determining between an in-bed state and an out-of bed state, based on the respiratory-signal variation; the body-movement determination means for determining the presence and level of a body movement, based on the respiratory-signal variation; the wake determination means and intervening-wake determination means for determining between a wake state and a sleep state, based on a determination result of the body-movement determination means; the sleep-initiation determination means for determining a sleep-initiation state having a transition from the wake state to the sleep state, based on the respiratory-signal variation, and the respective determination results of the in-bed/out-of-bed and wake determination means; the sleep determination means for determining a depth of sleep based on the respiratory-signal variation, and respective determination results of the in-bed/out-of-bed, body-movement, sleep-initiation and wake determination means; and the wake-up determination means for determining a wake-up state based on the respiratory-signal variation, and respective determination results of the in-bed/out-of-bed, body-movement, sleep-initiation, wake and sleep determination means. Thus, the sleep stage determination apparatus set forth in the second aspect of the present invention can combine a plurality of determination results to discriminate the sleep stages with enhanced creditability.

In the sleep stage determination apparatus set forth in the second aspect of the present invention, the in-bed/out-of-bed determination means may be operable, when the respiratory signal continues for a given time period or more at an amplitude equal to or greater than a given threshold value, to discriminate the in-bed state. This makes it possible to clearly distinguish between the in-bed state and the out-of-bed state and allow the subject to know the rhythm of sleep.

The body-movement determination means may be operable to discriminate one of a gross body movement state, a fine body movement state and a no body movement state, based on a plurality of threshold values assigned, respectively, to an amplitude fluctuation and amplitude level of the respiratory signal and a cycle of the respiratory signal. This makes it possible to accurately discriminate the body movements highly correlated with the sleep stages, based on the respiratory signal in a simplifying manner.

The wake determination means may be operable to discriminate one of a wake state, an unsteady state and a steady state, based on a variation of the body movement state within a given time period. This makes it possible to figure out rhythm between the wake state and the sleep state.

The intervening-wake determination means may be operable, when the body movement continues for a given time period or more at a given level or more, to discriminate the given time period of wake state. While the intervening-wake state (i.e. wake during sleep) otherwise is likely be discriminate as a sleep state, this intervening-wake determination means can accurately discriminate the intervening-wake state.

The sleep-initiation determination means may be operable to discriminate the wake state based on a transition pattern of an initial wake state and a variation pattern of the respiratory signal in a region around sleep initiation of the subject, to determine the sleep initiation state. This makes it possible to accurately discriminate a state when the subject starts falling to sleep, based on an actual sleep-initiation pattern of the subject.

The sleep-initiation determination means may include deep-sleep determination means for determining a deep sleep state, and REM-sleep/light-sleep determination means for determining a REM-sleep state and a light-sleep state. Further, the deep-sleep determination means may be operable, when each of a respiratory rate within a given time period, a fluctuation of the respiratory rate and a fluctuation of a respiratory cycle is equal to or less than a given threshold, and there is no body movement within a given time period, to discriminate the deep sleep state, and the REM-sleep/light-sleep determination means may be operable to make a determination based on comparing between a respiratory rate within a given time period and an average respiratory rate of the entire sleep states and counting a successive number of the given time periods, and a determination based on whether an apneic state is present or absent within the given time period, so as to discriminate the REM-sleep state and said light-sleep state in accordance with the determination results. This makes it possible to clearly discriminate between the plurality of sleep stages so as to provide highly-creditable sleep-stage determination data usable as a criterion for the quality of sleep.

In the sleep stage determination apparatus set forth in the second aspect of the present invention, the wake-up determination means may be operable, when no wake state appears before a given time period elapses from a time of the last determination of the wake state, to discriminate that the wake-up state occurs at the time of the last determination of the wake state. This makes it possible to accurately discriminate a state when the subject awakes, based on an actual wake-up pattern of the subject.

The sleep stage determination apparatus set forth in the first or second aspect of the present invention may further include the heartbeat signal detection means for detecting a heartbeat-related parameter, and the correction means for correcting the sleep stages using the detected heartbeat-related parameter. In this case, the sleep stages discriminated based on the respiratory signal is subjected to the correction using a variation of heart rate. Thus, differently from a case where the sleep stages are discriminated based on only a variation of heart rate, this sleep stage determination apparatus can discriminate the sleep stages with further enhanced creditability.

BEST MODE FOR CARRYING OUT THE INVENTION

Figure 1:
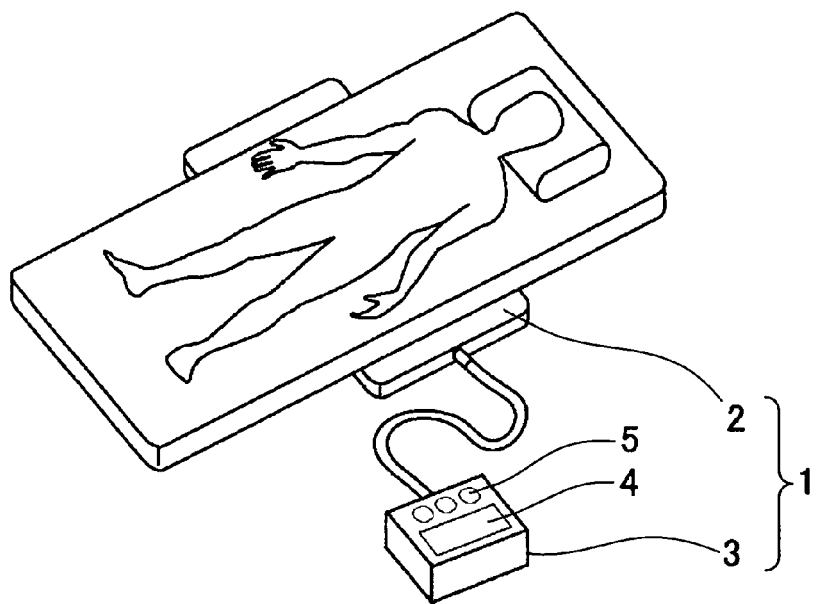
FIG. 1 is a perspective external view of a sleep stage determination apparatus according to one embodiment of the present invention, in a state when it is actually used.

A sleep stage determination apparatus according to a first aspect of the present invention comprises respiratory-signal detection means for detecting a variation of a respiratory signal from the body of a human subject, and sleep-stage determination means for determining a plurality of sleep stages using only the respiratory-signal variation.

In the sleep stage determination apparatus set forth in the first aspect of the present invention, the sleep-stage determination means may be operable to discriminate the sleep stages with respect to each of a plurality of unit zones defined by segmenting the respiratory-signal variation on a given time period basis.

Further, the sleep-stage determination means may be operable to discriminate the sleep stages in four classifications consisting of a wake stage, a deep sleep stage, a light sleep stage and a REM sleep stage.

A sleep stage determination apparatus according to a second aspect of the present invention comprises respiratory-signal detection means for detecting a variation in a respiratory signal from the body of a human subject, and sleep-stage determination means for determining a plurality of sleep stages using only the respiratory-signal variation. In this sleep stage determination apparatus, the sleep-stage determination means includes: in-bed/out-of-bed determination means for determining between an in-bed state and an out-of bed state, based on the respiratory-signal variation; body-movement determination means for determining the presence and level of a body movement, based on the respiratory-signal variation; wake determination means and intervening-wake determination means for determining between a wake state and a sleep state, based on a determination result of the body-movement determination means; sleep-initiation determination means for determining a sleep-initiation state having a transition from the wake state to the sleep state, based on the respiratory-signal variation, and the respective determination results of the in-bed/out-of-bed and wake determination means; sleep determination means for determining a depth of sleep based on the respiratory-signal variation, and respective determination results of the in-bed/out-of-bed, body-movement, sleep-initiation and wake determination means; and wake-up determination means for determining a wake-up state based on the respiratory-signal variation, and respective determination results of the in-bed/out-of-bed, body-movement, sleep-initiation, wake and sleep determination means.

In the sleep stage determination apparatus set forth in the second aspect of the present invention, the in-bed/out-of-bed determination means may be operable, when the respiratory signal continues for a given time period or more at an amplitude equal to or greater than a given threshold value, to discriminate the in-bed state.

The body-movement determination means may be operable to discriminate one of a gross body movement state, a fine body movement state and a no body movement state, based on a plurality of threshold values assigned, respectively, to an amplitude fluctuation and amplitude level of the respiratory signal and a cycle of the respiratory signal.

The wake determination means may be operable to discriminate one of a wake state, an unsteady state and a steady state, based on a variation of the body movement state within a given time period.

The intervening-wake determination means may be operable, when the body movement continues for a given time period or more at a given level or more, to discriminate the given time period of wake state.

The sleep-initiation determination means may be operable to discriminate the wake state based on a transition pattern of an initial wake state and a variation pattern of the respiratory signal in a region around sleep initiation of the subject, to determine the sleep initiation state.

The sleep-initiation determination means may include deep-sleep determination means for determining a deep sleep state, and REM-sleep/light-sleep determination means for determining a REM-sleep state and a light-sleep state.

Further, the deep-sleep determination means may be operable, when each of a respiratory rate within a given time period, a fluctuation of the respiratory rate and a fluctuation of a respiratory cycle is equal to or less than a given threshold, and there is no body movement within a given time period, to discriminate the deep sleep state.

The REM-sleep/light-sleep determination means may be operable to make a determination based on comparing between a respiratory rate within a given time period and an average respiratory rate of the entire sleep states and counting a successive number of the given time periods, and a determination based on whether an apneic state is present or absent within the given time period, so as to discriminate the REM-sleep state and said light-sleep state in accordance with the determination results.

The wake-up determination means may be operable, when no wake state appears before a given time period elapses from a time of the last determination of the wake state, to discriminate that the wake-up state occurs at the time of the last determination of the wake state.

With reference to the drawings, a sleep stage determination apparatus according to one embodiment of the present invention will now be described, where in the sleep stage determination apparatus is designed to discriminate a plurality of sleep stages using only a respiratory signal.

Figure 2:
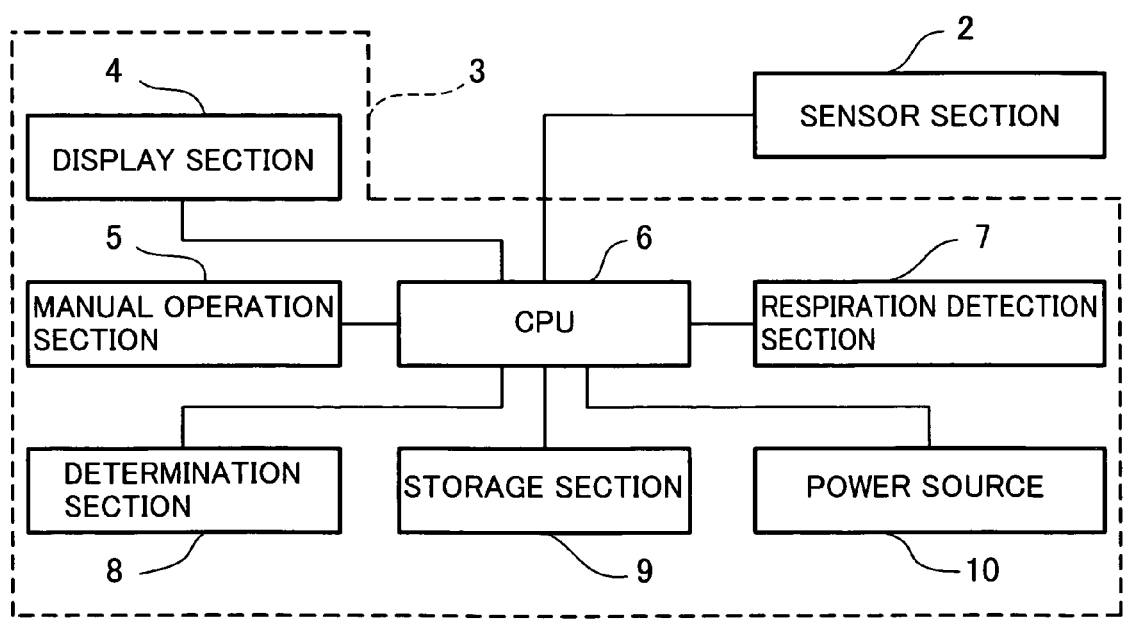
FIG. 2 is an electrical block diagram of the sleep stage determination apparatus according to the embodiment.

Firstly, with reference to FIGS. 1 and 2, the structure of the sleep stage determination apparatus according to this embodiment will be described below. FIG. 1 is a perspective external view of the sleep stage determination apparatus 1 during use, and FIG. 2 is an electrical block diagram thereof. In FIG. 1, the sleep stage determination apparatus 1 comprises a sensor section 2 for detecting a biological signal from the body of a human subject lying down on bedclothes, and a control box 3 electrically connected to the sensor section 2 and designed to discriminate a plurality of sleep stages. The control box 3 includes a display section 4 for indicating a sleep-stage determination result, guidance messages and other information, and a manual operation section 5 for allowing the subject or another operator to perform various manual operations, such as power on/off or measurement initiation/termination.

For example, the sensor section 2 may be designed to detect a pressure variation of an incompressible fluid enclosed in a mattress, using a capacitor microphone. In this case, the mattress is placed under the bedclothes to detect a biological signal from the subject lying in a face-up posture, as shown in FIG. 1.

As shown in FIG. 2, the control box 3 includes a CPU 6 electrically connected to the sensor section 2, the display section 4 and the manual operation section 5. The CPU 6 comprises a breathing or respiration detection section 7 for detecting a respiratory signal from a biological signal detected by the sensor section 2, a determination section 8 for performing various determination operations for determining the sleep stages, a storage section 9 for storing various conditional equations for the determination operations, a determination result and other data or information, and a power source 10 for supplying power to the sleep stage determination apparatus 1. In this embodiment, the CPU 6 internally has a control section for controlling the sleep stage determination apparatus 1, and a clock section for measuring time. The determination section 8 includes the following eight determination subsections for determining the sleep stages: an in-bed/out-of-bed determination subsection 11, a body-movement determination subsection 12, a wake determination subsection 13, a sleep-initiation determination subsection 14, a deep-sleep determination subsection 15, a REM-sleep/light-sleep determination subsection 16, an intervening-wake determination subsection 17 and a wake-up determination subsection 18. In this embodiment, the sleep stages to be discriminated by these determination subsections include four stages: a wake stage, a deep sleep stage, a light sleep stage and a REM sleep stage. Respective operations of the eight determination sections will be described later based on flowcharts.

Figure 3:
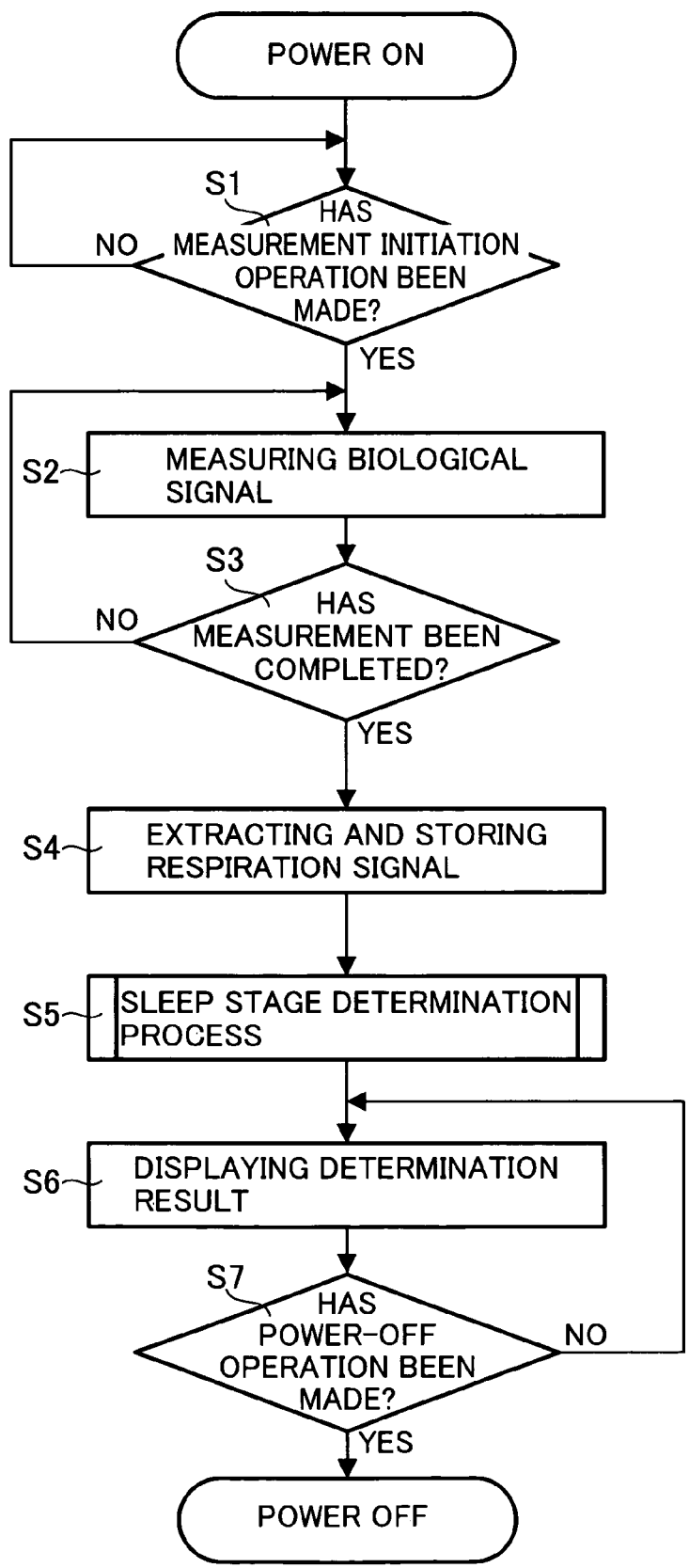
FIG. 3 is a flowchart showing a major operation of a sleep stage determination apparatus.
Figure 4:
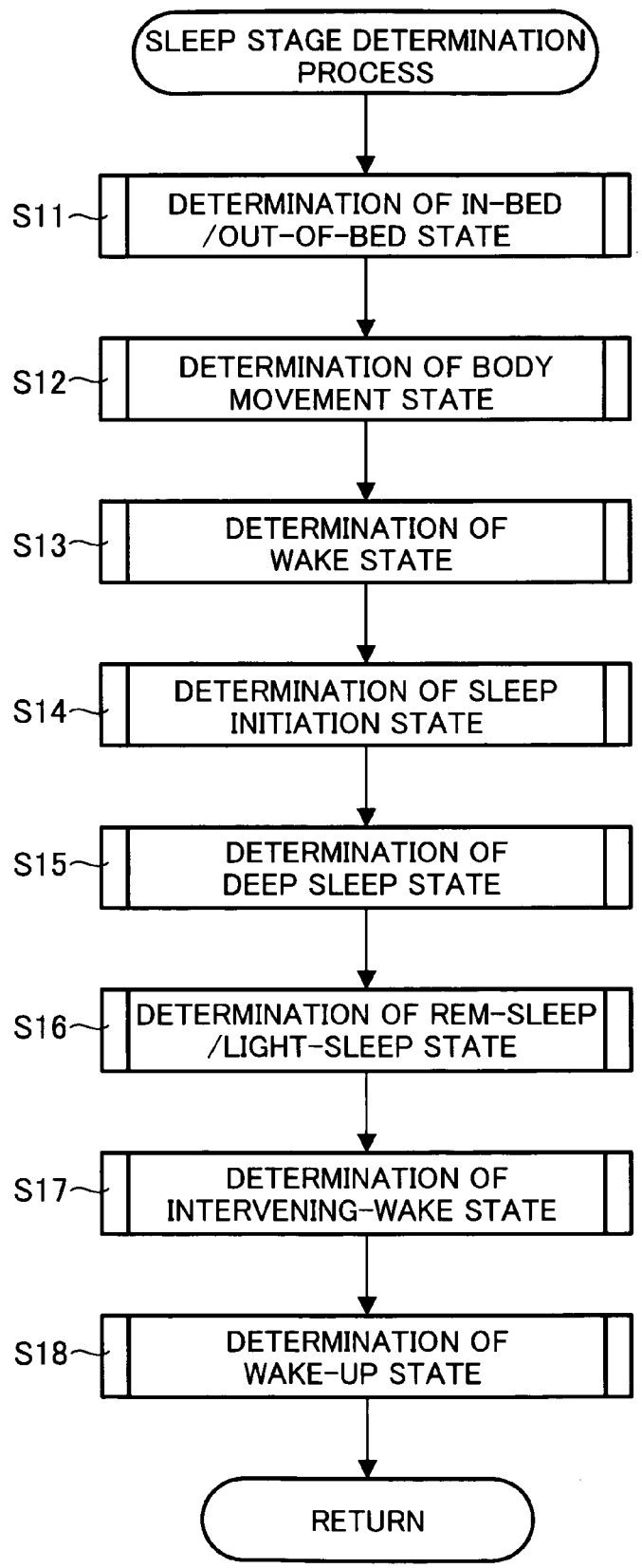
FIG. 4 is a flowchart showing a main routine of a sleep stage determination process.

With reference to the flowcharts of FIGS. 3 and 4, a major operation of the sleep stage determination apparatus 1 will be described below. FIG. 3 is a flowchart showing the major operation, and FIG. 4 is a flowchart showing a main routine of a sleep stage determination process configured to be performed using the above determination subsections 11 to 18.

As shown in FIG. 3, when the power source 10 of the sleep stage determination apparatus 1 is turned on in response to a manual operation for turning on a power switch or button of the manual operation section 5, a guidance message prompting a user or subject to lie down on a bed and manually operate the manual operation section 5 to initiate a measurement is indicated on the display section 4, and it is determined whether the measurement initiation operation has been made, in Step S1. If NO or no measurement initiation operation has been made, the Step S1 will be repeated to continue the indication of the guidance message. When the determination is YES or the measurement initiation operation has been made, the process advances to Step S2. In Step S2, a biological signal is detected by the sensor section 2, and stored as biological signal data on the storage section 9 together with a clock time measured by the built-in clock section of the CPU 6. In Step S3, it is determined whether the measurement has been completed. If NO or the measurement has not been completed, Step S2 will be repeated to continue the detection and storage of the biological signal. When the determination is YES or the measurement has been completed, the process advances to Step S4. In Step S4, the built-in control section of the CPU 6 instructs each of the sections to process the detected biological signal. Specifically, the biological signal data stored on the storage section 9 is read out, and a respiratory signal is detected from the biological signal data through the respiration detection section 7. Then, an amplitude and cycle of a waveform obtained from the respiratory signal are calculated and stored as respiratory data on the storage section 9. In this process, given that the aspiration signal is stored in zone units each having a given time period or duration (e.g. 30 seconds). The operation for calculating an amplitude and cycle of a waveform obtained from the respiratory signal has heretofore been known, and its detailed description will be omitted.

When the respiratory data is detected from the entire biological data stored on the storage section 9 and then stored on the storage section 9, each of the determination subsections 11 to 18 in the determination section 8 performs an after-mentioned sleep stage determination process, in Step S5.

Then, in Step S6, a result of the sleep stage determination process is indicated on the display section 4. In Step S7, it is determined whether an operation for turning off the power switch or button of the manual operation section 5 has been made. If NO or the operation for turning off the power switch or button has not been made, Step S6 will be repeated to continue the indication of the determination result. When the determination is YES or the operation for turning off the power switch or button has been made, the power source of the sleep stage determination apparatus 1 is turned off to complete the entire operation.

With reference to the flowchart of FIG. 4, the sleep stage determination process configured to be performed using the determination subsections 11 to 18 will be described below.

Under the control of the CPU 6, the determination section 8 is operable to sequentially perform the following determination process based on the aspiration data stored on the storage section 9 by the above unit zone in Step S4 illustrated in FIG. 3.

Specifically, the determination process is performed as follows. In Step S11, the in-bed/out-of-bed determination subsection 11 discriminates between an in-bed state and an out-of-bed state in a period from initiation of the measurement to termination of the measurement, based on a variation of the respiratory data. In Step S12, among a gross body movement state having a large movement, such as roll over (or turn over) in bed, a fine body movement state having a small movement, such as snoring, and a no body movement state obtained when a respiratory state is stable, the body-movement determination subsection 12 discriminates one of the body movement stated for each of the unit zones, based on an amplitude or cycle of a waveform obtained from the respiratory data. In Step S13, the wake determination subsection 13 discriminates whether a wake state is a well-defined wake state, based on the above discriminated body movement state. In Step S14, the sleep-initiation determination subsection 14 discriminates one of the unit zones where a wake state just after in-bed makes a transition to a sleep state (this unit zone will hereinafter be referred to as "sleep-initiation zone"). In Step S15, the deep-sleep determination subsection 15 discriminates whether the sleep state is a deep sleep state, based on the respiratory data variation and the above discriminated body movement state. In Step S16, the REM-sleep/light-sleep determination subsection 16 discriminates either one of a REM sleep state and a light sleep state, for each of the unit zones which are not discriminated as the deep sleep state. In Step S17, the intervening-wake determination subsection 17 discriminates whether a wake state is present or absent during the sleep state, based on a period of duration of a body movement. In Step S18, the wake-up determination subsection 18 discriminates one of the unit zones where the sleep state makes a transition to a wake-up state (this unit zone will hereinafter be referred to as "wake-up zone").

When the entire determination process is completed, the process returns to the major operation as shown in the flowchart of FIG. 3. Then, in Step S6, the wake state, the deep sleep state, the light sleep state and the REM sleep state, which have been discriminated through the above determination process, are indicated, respectively, as the wake stage, the deep sleep stage, the light sleep stage and the REM sleep state.

With reference to the flowcharts of FIG. 5 to 16, each operation of the determination subsections 11 to 18 will be described in order below. In the following description, a value of each constant indicated by an alphabetical character is determined based on a correlation between a sleep stage determination result obtained from polysomnographic data and an actual measurement data using the sleep stage determination apparatus 1.

With reference to the flowchart of FIG. 5, the operation of the in-bed/out-of-bed determination subsection 11 will be described below.

Given that a total number of unit zones defined by segmenting the respiratory data stored on the storage section 9 is "n-max", the operation of the in-bed/out-of-bed determination subsection 11 is performed for each of the unit zones from the 1st unit zone to the n-max-th unit zone. Thus, in Step S21, the "n" is initially set to "zero" (n=0). Then, in Step S22, the "n" is set to n+1 (n=n+1) to shift the unit zone to a next target unit zone, and the respiratory data corresponding to this target n-th unit zone is read from the storage section 9.

Given that a minimum value of a respiratory amplitude observed when a human subject lies in a face-up posture is A. In Step S23, it is discriminated whether a respiratory waveform in the target n-th unit zone satisfies the condition that an amplitude of the respiratory waveform equal to or greater than the value A continues for t (sec) or more (see FIG. 6), wherein each of A and t is a constant, and t<the unit time period). If YES or the respiratory waveform satisfies the above condition, the process advances to Step S24 based on the determination that the respiration is detected. In Step S24, it is determined that the subject is in the in-bed state, and the target n-th unit zone is discriminated as an in-bed zone. Then, in Step S25, the determination result is stored on the storage section 9 in association with the target n-th unit zone. When the determination result is NO or the respiratory waveform does not satisfy the above condition, the process advances to Step S27. In Step S28, it is determined that the subject is in the out-of-bed state, and the target n-th unit zone is discriminated as an out-of-bed zone. Then, in Step S25, the determination result is stored in the same manner as described above. In Step S26, it is determined whether all of the unit zones have been subjected to the in-bed/out-of-bed determination process, or whether n=n-max. If NO or all of the unit zones have not been fully subjected to the in-bed/out-of-bed determination process, the process returns to Step S22. In Step S22, the "n" is set to n+1 (n=n+1), and the in-bed/out-of-bed determination process will be repeated. Subsequently, when the determination in Step S26 becomes YES or all of the unit zones have been subjected to the in-bed/out-of-bed determination process, the process returns to the main routine illustrated in the flowchart of FIG. 4, and advances to the next determination subroutine.

Figure 7:
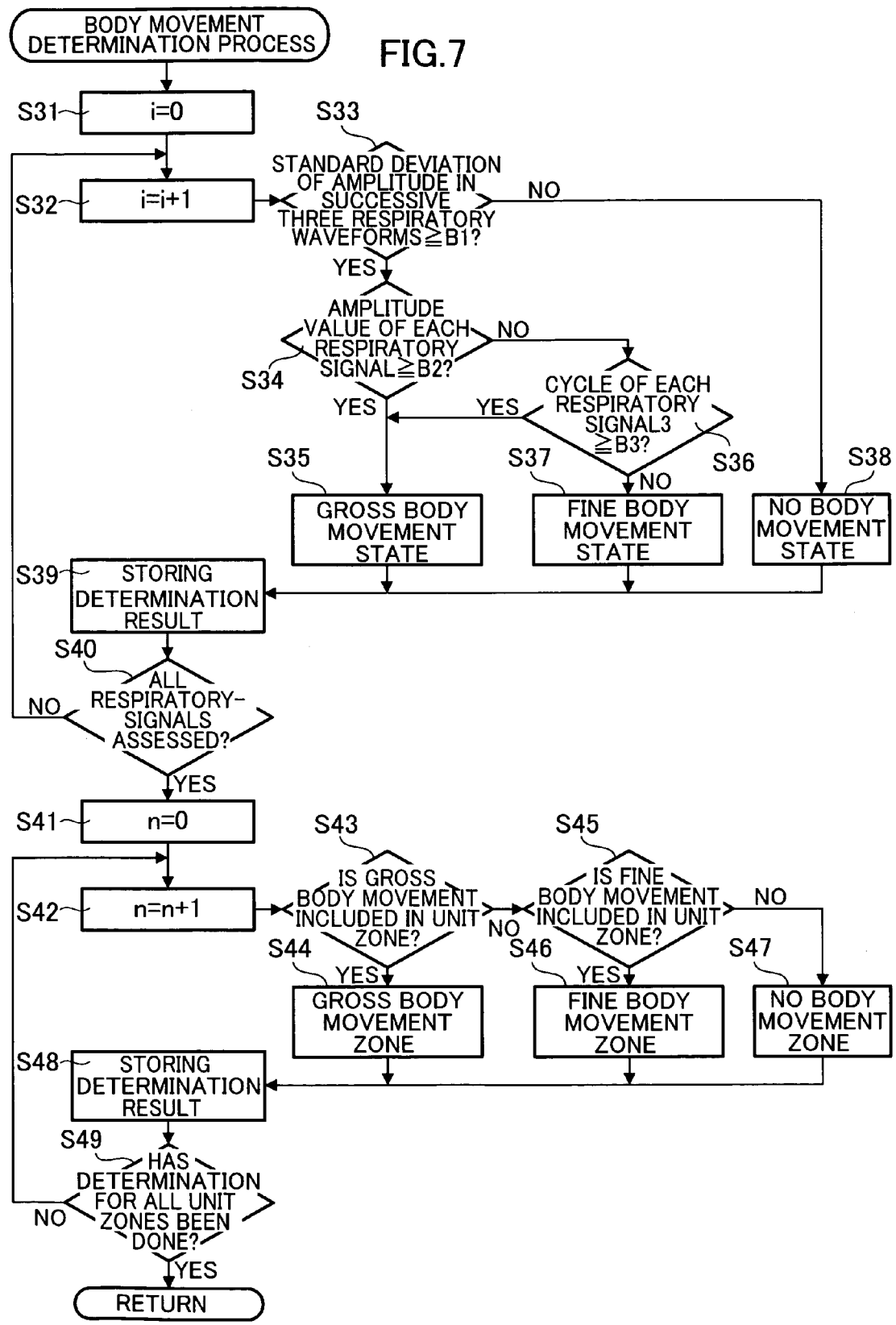
FIG. 7 is a flowchart showing a subroutine of a body-movement determination process.
Figure 8:
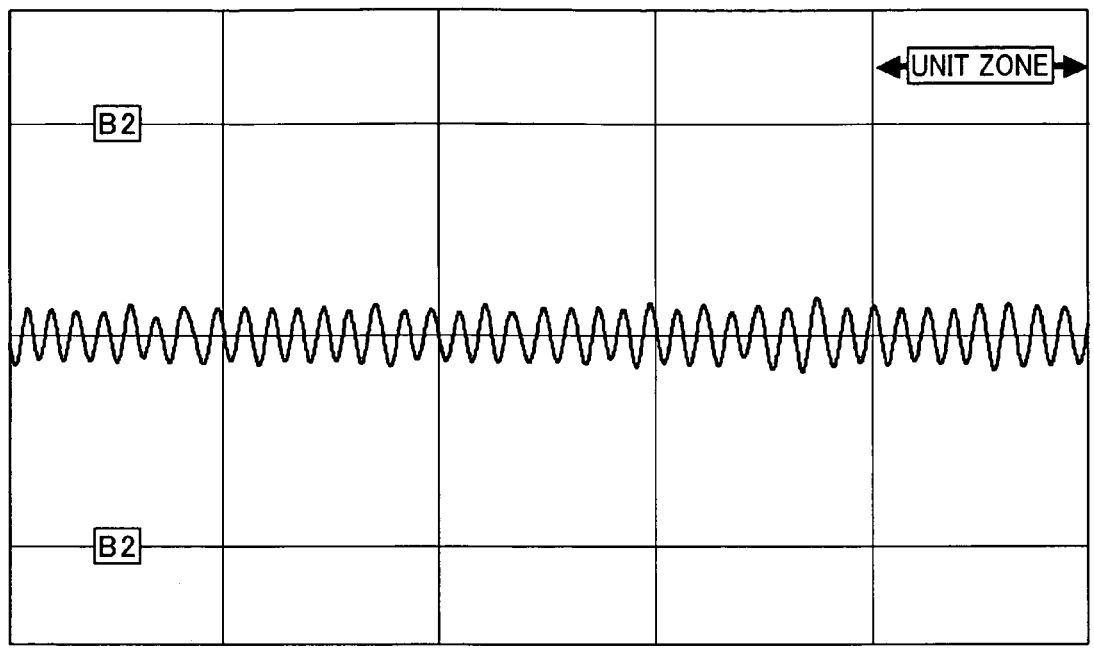
FIG. 8 is a waveform chart showing a respiratory waveform in a no body movement state.
Figure 9:
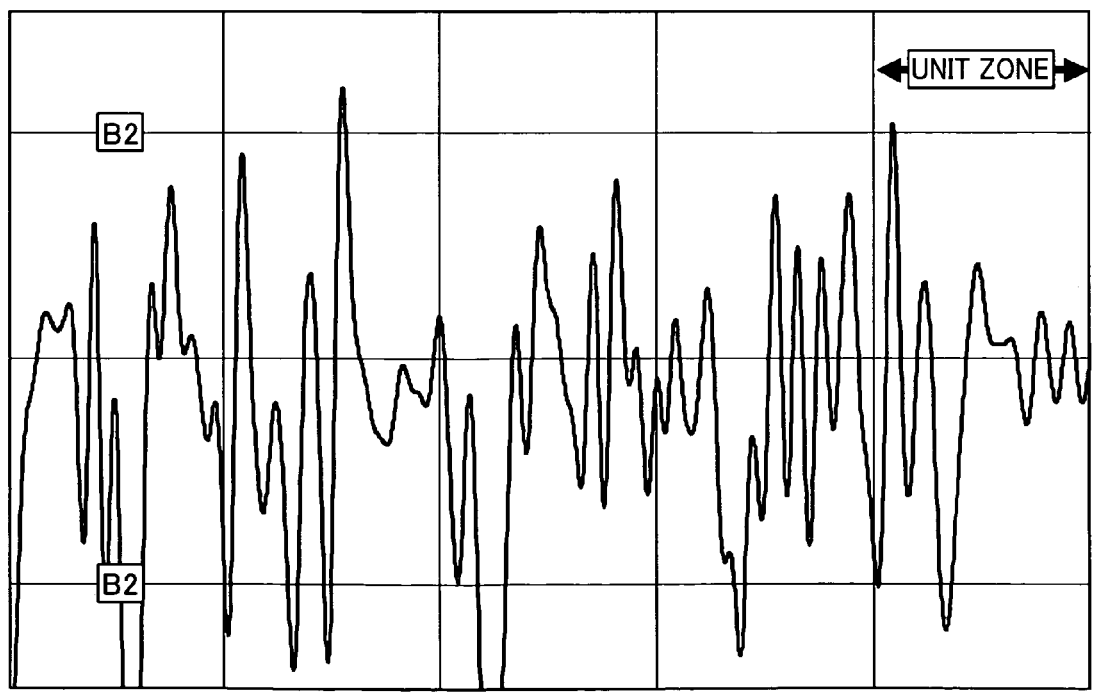
FIG. 9 is a waveform chart showing a respiratory waveform in a gross body movement state.
Figure 10:
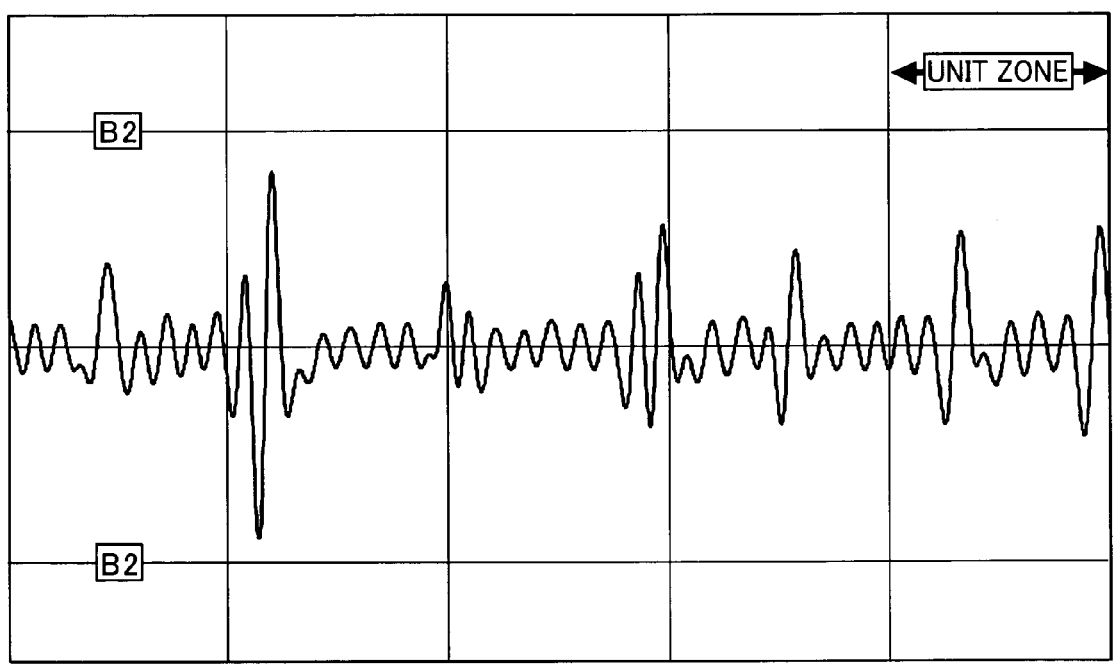
FIG. 10 is a waveform chart showing a respiratory waveform in a fine body movement state.

With reference to the flowchart of FIG. 7, the operation of the body-movement determination subsection 12 will be described below.

The body-movement determination subsection 12 is operable to discriminate the presence and level of a body movement, based on the amplitude of the respiratory signal waveform irrespective of n-th of the unit zones, and then discriminate one of the body movement states for the specific n-th unit zone which is discriminated that a body movement is present therein.

Given that a total number of respirations in a period from the initiation to the completion of the measurement is i-max. Thus, in Step S31, the "i" is initialized to zero (i=0). Then, in Step S32, the "i" is set to i+1 (i=i+1) to advance the respiration number by one, and the respiratory waveform corresponding to the i-th respiration in order from the 1st respiration to the i-max-th respirations is read out from the storage section 9.

In Step S32, the two respiratory waveforms corresponding to the i+1-th respiration and the i+2-th respiration are further read out. Then, in Step S33, the presence of a body movement is discriminated based on a fluctuation in respective amplitudes of the three respiratory waveforms corresponding to the i-th, i+1-th and i+2-th respirations. Specifically, it is determined whether a standard deviation of the amplitudes of the three respiratory waveforms≧B1 (wherein B1 is a constant representing a threshold value determining whether the respiratory waveforms are stable). If NO or the standard deviation<B1, the process advances to Step S38. In Step S38, in view of a small fluctuation in respiratory rate or stability in the respiratory waveforms, a body movement state indicated by the i+1-th respiration in the successive three respiratory waveforms is discriminated as the no body movement state (see FIG. 8). If the determination in Step S33 is YES or the standard deviation≧B1, it is determined that the i+1-th respiration indicates the presence of a body movement in view of a large fluctuation in respiratory rate, and the process advances to Step S34. In Step S34, it is determined whether the i+1-th respiratory waveform has an amplitude value≧B2 (wherein B2 is a maximum value of a respiratory amplitude observed when a human subject lies in a normal face-up posture, and a constant satisfying B2>A). If YES or the amplitude value≧B2, the process advances to Step S35. In Step S35, a body movement state indicated by the i+1-th respiration is discriminated as the gross body movement (see FIG. 9). If NO or the amplitude value<B2, the process advances to Step 36. In Step S36, the level of the body movement is discriminated based on a cycle of the respiratory waveform. Specifically, it is determined whether the i+1-th respiration has a cycle≧B3. If YES or the cycle≧B3, a body movement state indicated by the i+1-th respiration is discriminated as the gross body movement, in Step S35. If NO or the cycle<B3, the process advances to Step S37. In Step S37, in view of the waveform having a low amplitude, a short cycle and a large fluctuation, a body movement state indicated by the i+1-th respiration is discriminated as the fine body movement (see FIG. 10).

In this manner, the gross body movement, fine body movement and no body movement states are discriminated from each other. Then, in Step S39, the determination result is stored on the storage section 9 in association with the corresponding i-th respiration. In Step S40, it is determined whether all of the respirations have been subjected to the body-movement determination process, or the determination for the i-max-th respiration has been done. If NO or all of the respirations have not been fully subjected to the body-movement determination process, the process returns to Step S32 so as to set the respiration number to i+1 (i=i+1), and the body-movement determination process will be repeated. When all of the respirations have been subjected to the body-movement determination process, the process advances to Step S41 so as to perform a body-movement determination process for each of the unit zones in Step S41 and subsequent Steps.

Figure 5:
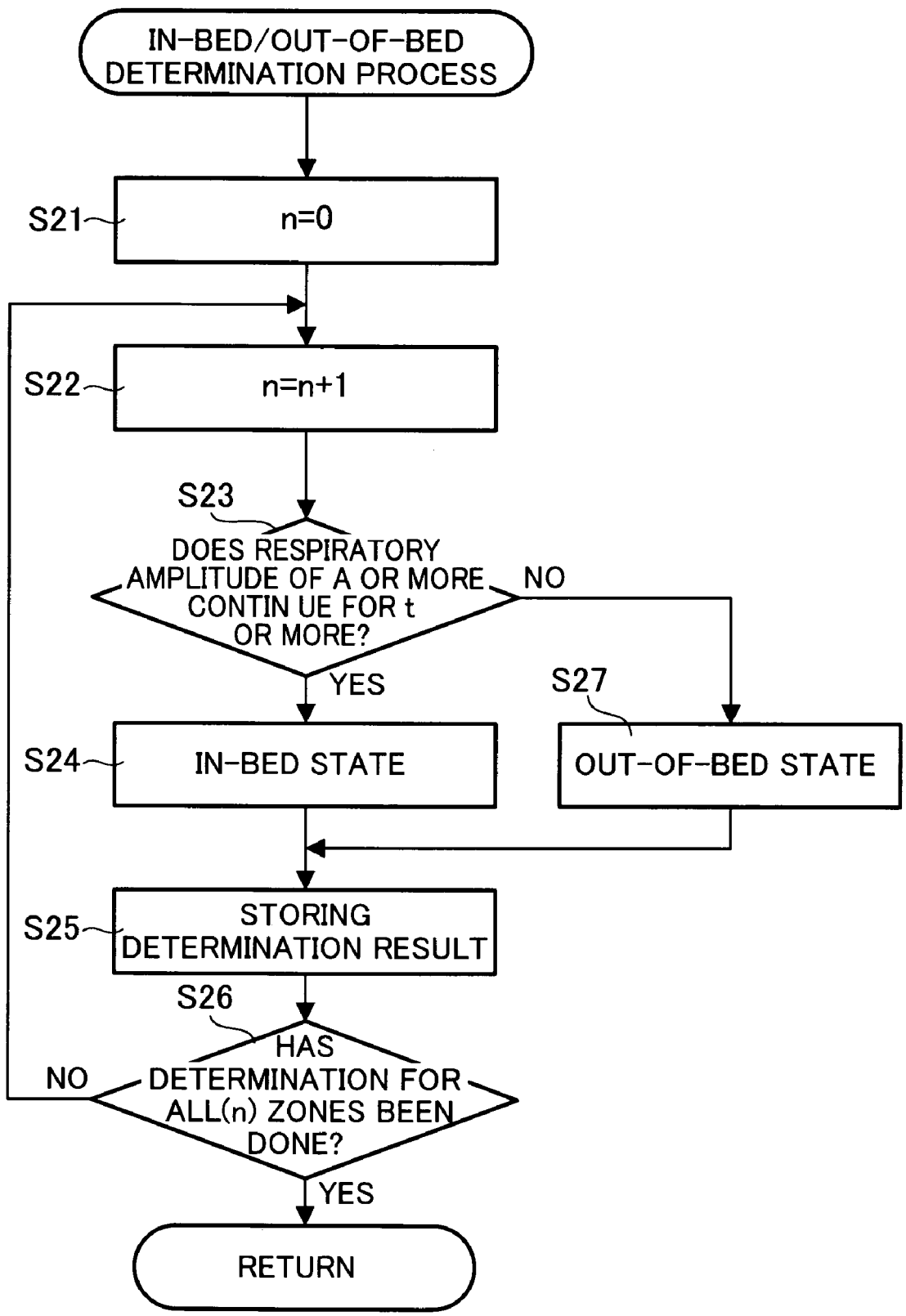
FIG. 5 is a flowchart showing a subroutine of an in-bed/out-of-bed determination process.
Figure 6:
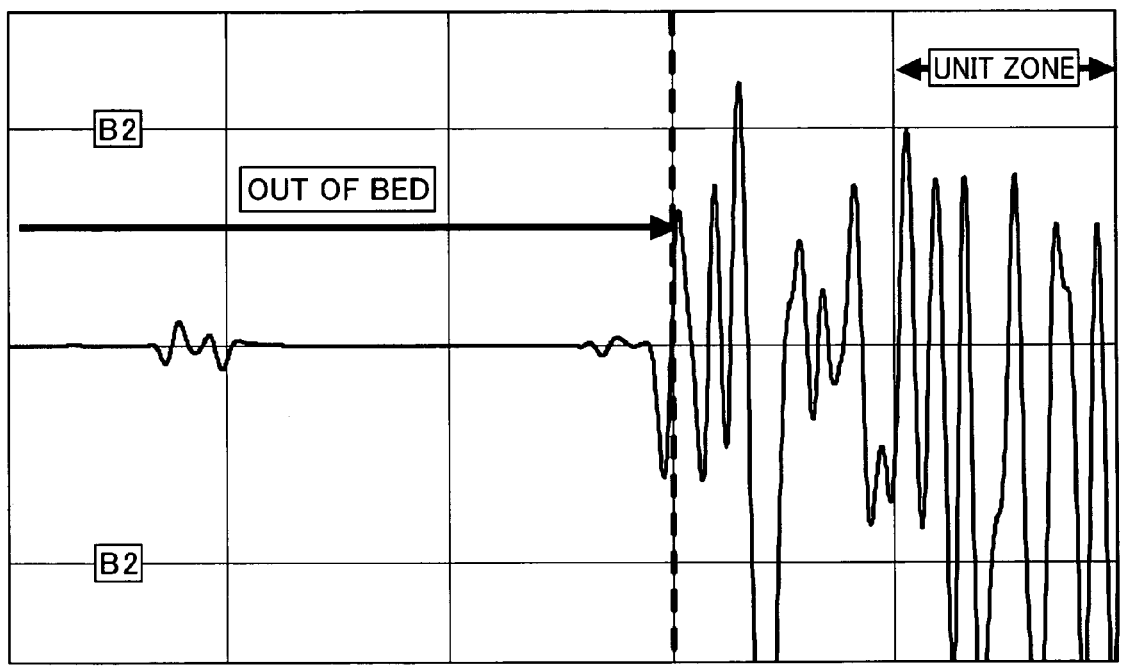
FIG. 6 is a graph showing a respiratory waveform in an out-of-bed state.

Specifically, in the same manner as that in Steps S21 and S22 in FIG. 5, the "n" is initialized to zero (n=0), in Step S41, and then set to n+1 (n=n+1) to read the respiratory data corresponding to this target n-th unit zone, in Step S42. In Step S43, it is discriminated whether the read or target n-th unit zone has a specific respiratory waveform discriminated as the gross body movement state. If YES or the target n-th unit zone has the specific respiratory waveform, the target n-th unit zone is discriminated as a gross body movement zone, in Step S44. If NO, or the target n-th unit zone does not have such a specific respiratory waveform, the process advances to Step S45. In Step S45, it is discriminated whether the target n-th unit zone has a specific respiratory waveform discriminated as the fine body movement state. If YES or the target n-th unit zone has the specific respiratory waveform, the target n-th unit zone is discriminated as a fine body movement zone, in Step S46. If NO, or the target n-th unit zone does not have such a specific respiratory waveform, target n-th unit zone is discriminated as a no body movement zone, in Step S47.

In this manner, the gross body movement zone, the fine body movement zone and the no body movement zone are discriminated from each other. Then, in Step S48, the determination result is stored on the storage section 9 in association with the corresponding n-th respiration. In Step S49, it is determined whether all of the unit zones have been subjected to the body-movement determination process. If NO or all of the unit zone have not been fully subjected to the body-movement determination process, the process returns to Step S42 so as to set the unit zone number to n+1 (n=n+1), and the body-movement determination process for each of the unit zones will be repeated. When all of the unit zones have been subjected to the body-movement determination process, the process returns to the main routine illustrated in the flowchart of FIG. 4, and advances to the next determination subroutine.

Figure 12:
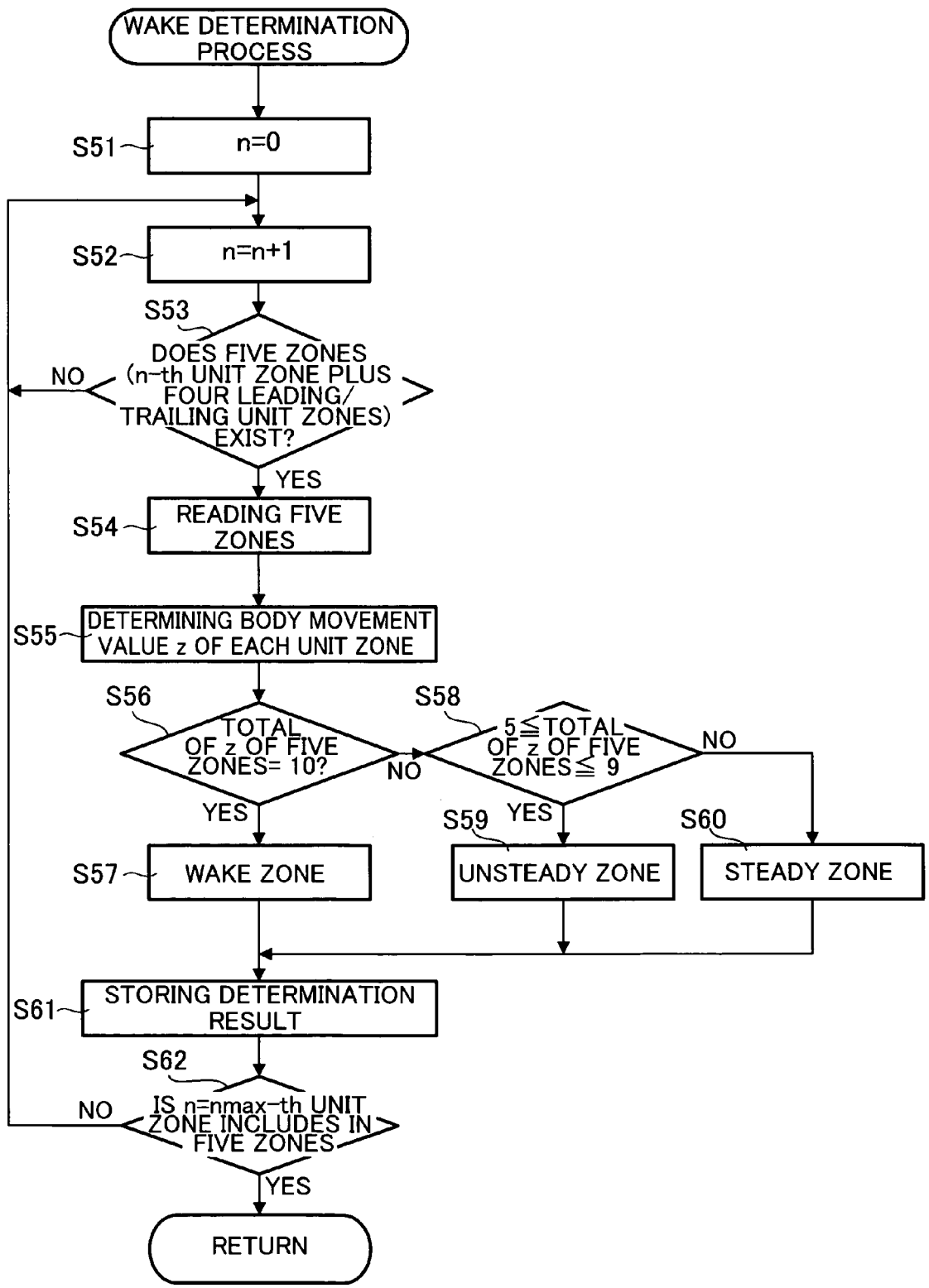
FIG. 12 is a flowchart showing a subroutine of the wake determination process.

With reference to the flowchart of FIG. 12, the operation of the wake determination subsection 13 will be described below.

Figure 11:
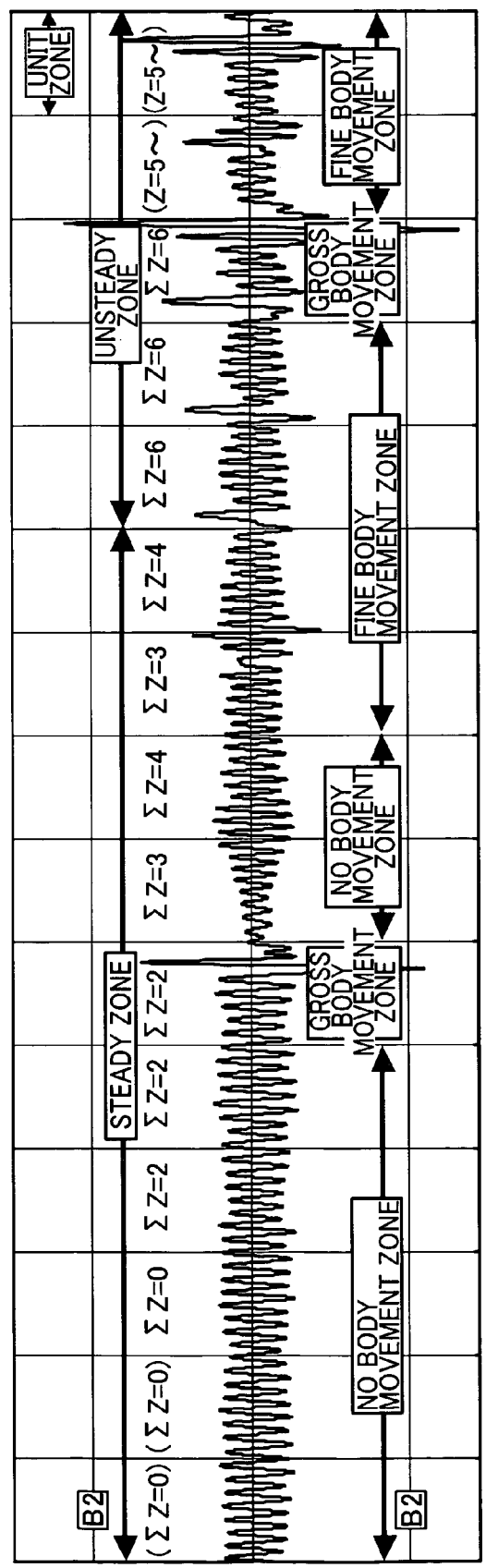
FIG. 11 is a waveform chart showing a relationship between the body-movement determination process and a wake determination process.

In order to perform a wake determination process on an unit zone-by-unit zone basis as in the above processes, in Step S51, the "n" of the unit zone is initialized to zero (n=0), and respiratory data corresponding to this target n-th unit zone is read out. Then, as shown in FIG. 11, in Step S53, it is determined whether a total five unit zones consisting of the read n-th unit zone, two adjacent leading unit zones and two adjacent trailing unit zones exist in the storage section 9. If NO or the storage section 9 does not have such unit zones, the process returns to Step S52 so as to set the "n" to n+1 (n=n+1). If YES or the five unit zones exist in the storage section 9, the process advances to Step S56 so as to read the five unit zones from the storage section 9. Then, Step S55, a body movement value Z for each of the five unit zones is determined. Based on the body movement zone discriminated by the body-movement determination subsection 12 described in detail in connection with FIG. 7, the body movement value Z is determined to be "2" for the gross body movement zone, "1" for the fine body movement zone and "0 (zero)" for the no body movement zone. Further, a sum of the above body movement values z of the five unit zones (wherein 0≦total of Z≦10; the total of Z will hereinafter be occasionally expressed as "Σ Z") is calculated.

In Step S56, it is determined whether the sum of the body movement values Z of the five unit zones is 10. If YES or the sum of Z is 10, the process advances to Step S57. In Step S57, the n-th unit zone read out in Step S52 (unit zone at the center of the five unit zones) is discriminated as a wake zone which is in the wake state, because each of these five unit zones is the gross body movement zone. If NO or the sum of Z is less than 10, the process advances to Step S58. In Step S58, If YES or the sum of Z is 10, the process advances to Step S57. In the same manner as that in Step S56, it is determined whether 5≦total of Z≦9. If YES or the total of Z falls within this range, the n-th unit zone is discriminated as an unsteady zone having a high possibility that it is in the REM sleep or light sleep state when the respiratory state is relative unstable, in Step S59. If NO or the total of Z does not fall within the above range, specifically, the total of Z≦4, the n-th unit zone is discriminated as a steady zone having a high possibility that it is in the deep sleep or light sleep state when the respiratory state is relative stable, in Step S60.

In this manner, the wake zone, the unsteady zone and the steady zone are discriminated. Then, in Step 61, the determination result is stored on the storage section 9 in association with the corresponding n-th unit zone. In Step S62, it is determined whether the n-max-th unit zone is included in the five unit zones. If NO or the n-max-th unit zone is not included in the five unit zones, the process returns to Step S52 so as to set the "n" to n+1 (n=n+1), and the wake determination process for each of the unit zones will be repeated. If YES or the n-max-th unit zone is included in the five unit zones, the process returns to the main routine, and advance to the next determination subroutine.

With reference to the flowchart of FIG. 13, the operation of the sleep-initiation determination subsection 14 will be described.

In addition to the wake determination operation of the wake determination subsection 13 described in detail in connection with FIG. 12, with a view to determining the unit zone where an initial wake state just after in-bed makes a transition to a sleep state (this unit zone will hereinafter be referred to as "sleep-initiation zone"), the sleep-initiation determination subsection 14 is operable to more specifically discriminate the initial wake zone based on a sleep initiation pattern of the subject so as to define the sleep-initiation zone.

In order to perform an sleep-initiation determination process on an unit zone-by-unit zone basis as in the above processes, in Step S71, the "n" of the unit zone is initialized to zero (n=0), and respiratory data corresponding to this target n-th unit zone is read out. Then, in Step S73, it is determined whether the read or target n-th unit zone is the unsteady zone described in detail in connection with FIG. 12. This unsteady zone means the first unsteady zone which appears after continuation of the initial wake zone. Thus, if NO or the target n-th unit zone is not the unsteady zone, the process will be repeated from Step S72 until the unsteady zone is read. Even if the n-th unit zone is determined to be the unsteady zone in Step S73, it is quite unlikely that the steady state suddenly appears just after in-bed without going through the initial wake state and the unsteady state, in respirations of a normal human subject. Thus, it is easily presumable that such a steady zone is low-creditable data, and it is reasonable to redefine it as a wake zone.

If YES or the target n-th unit zone is the unsteady zone, the process advances to Step S74. In Step S74, it is determined whether the unit zone discriminated as the wake zone is not included within a given number C1 of unit zones from the target n-th unit zone. Given that the target n-th unit zone is the sleep-initiation zone, it is quite unlikely to wake just after initiation of sleep, in sleep of a human subject. The given number C1 is a constant defining a range where a human subject is generally unlikely to wake just after initiation of sleep. Thus, if the determination in Step 74 is NO or the wake zone exists within a given number C1 of unit zones from the target n-th unit zone, the target n-th unit zone is stored after redefining it as the wake zone, and the process will be repeated from Step S72. If YES or the wake zone does not exist, the target n-th unit zone is discriminated as a (tentative) sleep-initiation zone in Step S75. Then, in Step S77 and subsequent Steps, the sleep-initiation zone will be more accurately discriminated.

A process in Step S77 and subsequent Steps is designed to determine a range to be considered as and redefined as the wake zone, in the unit zones discriminated as the unsteady zone after the (tentative) sleep-initiation zone, based on three respiratory variation patterns in a region around sleep initiation of a human subject, which have been developed through actual experimental tests, by the inventor, so as to define the unit zone just after the determined range, as the sleep-initiation zone.

Specifically, in Step S77, a range of from the earliest one of the unit zones discriminated as the in-bed zone after initiation of the measurement by the in-bed/out-of-bed determination subsection 11 described in detail in connection with FIG. 5, to the unit zone just before the (tentative) sleep-initiation zone, is determined as a reference range. Then, in the reference range, a variance $\sigma^2$ in respiratory rate (the number of respirations) in each of the unit zones is calculated. Further, three ranges each including the reference range and extending from the (tentative) sleep-initiation zone by a corresponding one of given zone numbers $\alpha$, $\beta$ and $\gamma$ (wherein $\alpha$, $\beta$ and $\gamma$ satisfy the following relation: $\alpha<\beta<\gamma$, and each of $\alpha$, $\beta$ and $\gamma$ is determined based on an experimentally-obtained time period suitable for determining a corresponding one of the above three respiratory variation patterns) are defined, respectively, as a range $\alpha$, a range $\beta$ and a range $\gamma$, and a variance in respiratory rate in each of the ranges $\alpha$, $\beta$ and $\gamma$ are calculated, and the calculated variances are expressed, respectively, as $\sigma\alpha^2$, $\sigma\beta^2$ and $\sigma\gamma^2$. The three respiratory variation patterns are discriminated using, respectively, as a condition D, a condition E and a condition F, which are defined based on the variances $\sigma^2$, $\sigma\alpha^2$, $\sigma\beta^2$ and $\sigma\gamma^2$.

In a first one of the respiratory variation patterns, a fluctuation of respirations of the subject quickly lowers and then a transition to the sleep state occurs. Thus, in Step S78, the first respiratory variation pattern is discriminated using the condition D defined by the following formulas: "$\sigma\alpha^2 > \sigma\beta^2$ (Formula 1)" and "$\sigma\beta^2 \leq C2$ (Formula 2)". That is, a fluctuation of respirations quickly reduces along with extension of the range, as shown in the Formula 1, and a variance to be caused by increase in number of the unit zones is less than the given number C2, as shown in the Formula 2. The number C2 is a constant allowing for determining such that the first respiratory variation pattern is significantly close to a fluctuation in respiratory rate appearing after initiation of sleep. When the condition D is satisfied, it may be discriminated that the range $\beta$ is already in the sleep state.

Thus, if the determination result in Step S78 is YES or the condition D is satisfied, it is determined that the wake zone extends up to at least the range $\alpha$, and the unit zone just after the range $\alpha$ is determined as the sleep-initiation zone. If the determination result is NO or the condition D is not satisfied, the determination about a second one of the respiratory variation patterns is performed.

In the second respiratory variation pattern, a fluctuation of respirations of the subject gradually lowers and then a transition to the sleep state occurs. Thus, in Step S80, the second respiratory variation pattern is discriminated using the condition E defined by the following formulas: "$\sigma^2 \times C3 \geq \sigma$ $\alpha^2 \geq \sigma \beta^2$ (Formula 3)", wherein C3 is a constant satisfying the following relation: C3<1. The constant C3 is set to reduce some percentages of a fluctuation in the reference range. Further, there is the following relation with C2 in the Formula 2: $\sigma^2 \times C3 > C2$. Thus, as shown in FIG. 3, a fluctuation in the range $\alpha$ is equal to or less than the fluctuation in the reference range reduced by C3, and a fluctuation in the range $\beta$ is equal to or less than the fluctuation in the range $\alpha$.

Thus, if the determination result in Step S80 is YES or the condition E is satisfied, the process advances to Step S79. In Step 79, it is determined that the wake zone extends up to the range $\beta$, because the fluctuation tends to become lower even though the pace is very slow, and the unit range just after the range $\beta$ is determined as the sleep-initiation zone. If the determination result is NO or the condition E is not satisfied, the determination about a third one of the respiratory variation patterns is performed.

In the third respiratory variation pattern, a fluctuation of respirations of the subject increases as compared with that in the reference range, and then lowers. Thus, in Step S81, the third respiratory variation pattern is discriminated using the condition F defined by the following formulas: "$\sigma^2 < \sigma \beta^2$ (Formula 4)" and "$\sigma \gamma^2 < \sigma \beta^2$ (Formula 5)". As compared with the conditions D, E, this pattern is observed for a relatively long span. Thus, the range $\beta$ and the range $\gamma$ are used in this formula.

Thus, if the determination result in Step S81 is YES or the condition F is satisfied, it is determined that the wake zone extends up to at least the range $\beta$ having an increased fluctuation within the range $\gamma$, and the unit zone just after the range $\beta$ is determined as the sleep-initiation zone.

If the determination result is NO or the condition F is not satisfied, the process advances to Step S82. That is, the process advances to Step S82 only if none of the conditions D, E and F are satisfied. In Step S82, each of the zone numbers $\alpha$, $\beta$ and $\gamma$ is increased by a zone number $\delta$ to determine new ranges $\alpha$, $\beta$ and $\gamma$. Then, the process returns to Step S78, and Steps S78 to S81 using the conditions D, E, F will be repeated until the sleep-initiation zone is determined.

If the sleep-initiation zone is determined in Step S79, the wake zone and sleep-initiation zone are stored in association with the corresponding n-th unit zone, and the process retunes to the main routine illustrated in the flowchart of FIG. 4, and advances to the next determination subroutine.

Figure 14:
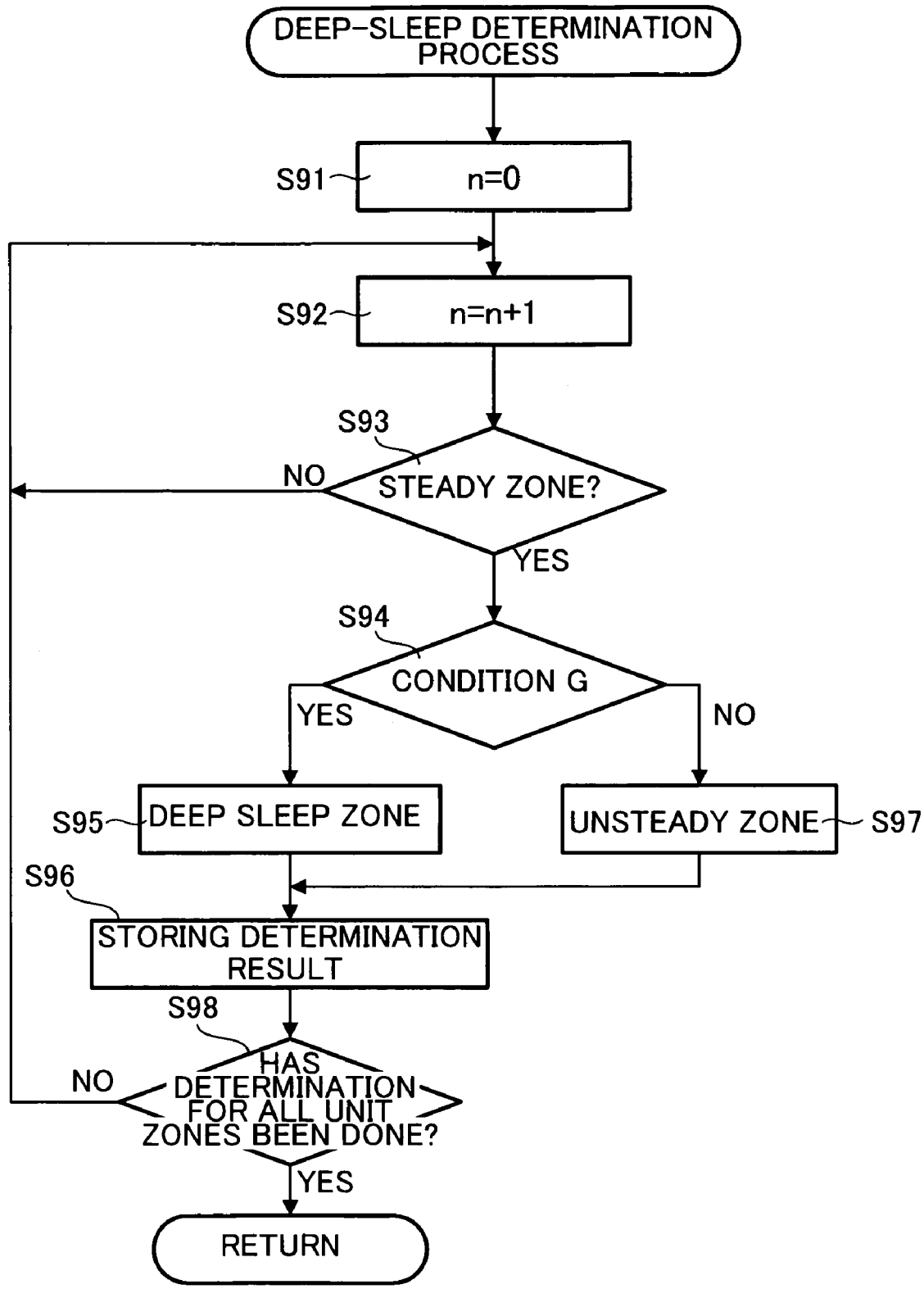
FIG. 14 is a flowchart showing a subroutine of a deep-sleep determination process.

With reference to FIG. 14, the operation of the deep-sleep determination subsection 15 will be described.

In the deep sleep state, the rhythm of respirations becomes gentle and constant, and substantially no body movement occurs. Thus, the following determination process will be performed.

In order to perform a deep-sleep determination process on an unit zone-by-unit zone basis as in the above processes, in Step S91, the "n" of the unit zone is initialized to zero (n=0). In Step S92, the "n" is set to n+1 (n=n+1), and respiratory data corresponding to this target n-th unit zone is read out. Then, in Step S93, it is determined whether the read or target n-th unit zone is the stable zone described in detail in connection with FIG. 12. If the target n-th unit zone is not the stable zone, the process returns to Step S92 so as to set the "n" to n+1 (n=n+1), and the process will be repeated until the unit zone corresponding to the stable zone is read out. If the determination in Step S93 is YES, a determination using a condition G arranged by combining a plurality of criterions is performed in Step S94.

The condition G includes five conditions: "a respiratory rate in an n-th unit zone$\leq$H1", "an average deviation of a cycle of a respiratory waveform in the n-th unit zone$\leq$H2", "a difference between respective respiratory rates in the n-th unit zone and an n+1-th or n-1-th unit zone$\leq$H3" and "the n-th unit zone is the no body movement zone", wherein each of H1, H2 and H3 is a constant to be determined through an actual experimental test). When all of the five conditions are satisfied, the n-th unit zone is discriminated as the deep sleep zone.

Thus, if the determination in Step S94 is YES or the target n-th unit zone satisfies the condition G, the process advances to Step S95. Then, the target n-th unit zone is discriminated as the deep sleep zone in Step S95, and stored on the storage section 9 in Step S96. If the determination in Step S94 is NO or the target n-th unit zone does not satisfy the condition G, the process advances to Step S97. Then, the target n-th unit zone is discriminated as the unsteady zone in Step S97, and redefined as the unsteady zone and stored on the storage section 9 in Step S96. In Step S98, it is determined whether all of the unit zones have been subjected to the deep-sleep determination process. If NO or all of the unit zones have not been completely subjected to the deep-sleep determination process, the process will be repeated from Step S92. If YES or all of the unit zones have been subjected to the deep-sleep determination process, the process returns to the main routine illustrated in the flowchart of FIG. 4, and advances to the next determination subroutine.

Figure 15:
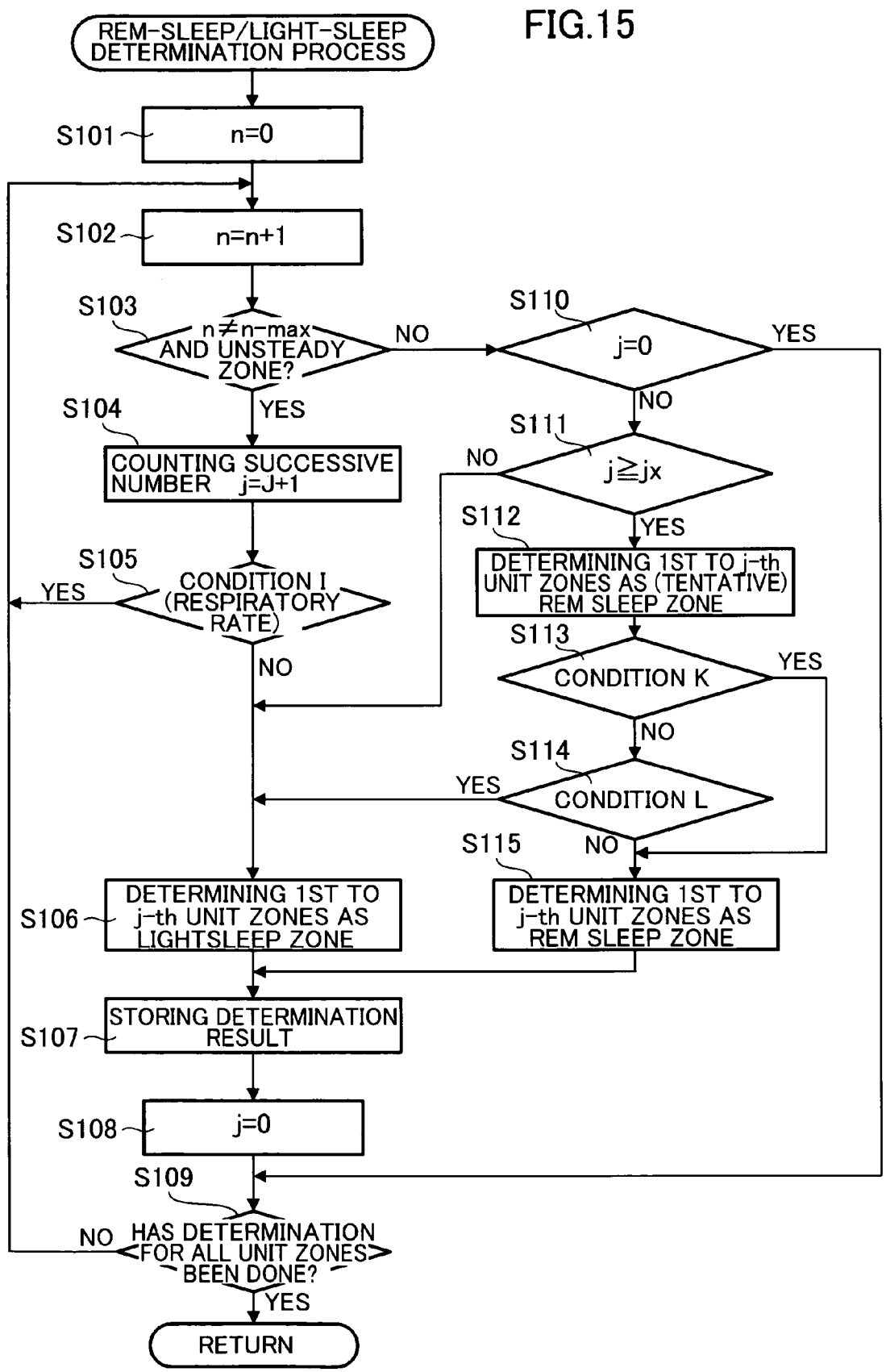
FIG. 15 is a flowchart showing a subroutine of a REM-sleep/light-sleep determination process.

With reference to the flowchart of FIG. 15, the operation of the REM-sleep/light-sleep determination subsection 16 will be described.

In the REM sleep state, an increase and fluctuation in respiratory rate continuously occur, and the number of body movements increases. Thus, the following REM-sleep/light-sleep determination process will be performed.

In order to perform the REM-sleep/light-sleep determination process on an unit zone-by-unit zone basis as in the above processes, in Step S101, the "n" of the unit zone is initialized to zero (n=0). In Step S102, the "n" is set to n+1 (n=n+1), and respiratory data corresponding to this target n-th unit zone is read out.

In Step S103, it is determined whether the read or target n-th unit zone is not the n-max-th unit zone (n$\neq$n-max), and is the unsteady zone described in detail in connection with FIG. 12. If YES or the target n-th unit zone is not the n-max-th unit zone (n$\neq$n-max) and is the unsteady zone, the process advances to Step S104. In Step S104, a successive number j of the unsteady zones is counted in a manner of j=j+1. Then, in Step S105, it is determined whether the target n-th unit zone satisfies a condition I of "an average of respiratory rates of the respective unit zones in the entire in-bed zone$\leq$a respiratory rate of the target n-th unit zone". That is, it is determined whether the respiratory rate of the target n-th unit zone is greater than an average respiratory rate during sleep, in view of the aforementioned phenomenon that a respiratory rate increases in the REM sleep state.

If the determination in Step S105 is NO or the condition I is not satisfied, each unit zone having a successive number j=1 to j is discriminated as a light sleep zone in Step S106. If the determination in Step S105 is YES or the condition I is satisfied, the process returns to Step S102 so as to set the "n" to n+1 (n=n+1), and repeat the operation for detecting the unsteady zone.

If the determination in Step S103 or the target n-th unit zone is the n-max-th unit zone (n=n-max) or is not the unsteady zone, it is determined whether a succession number of the unsteady zones is zero (j=0), in Step S110. If YES or j=0, the process returns to Step S102 so as to set the "n" to n+1 (n=n+1), and the above Steps will be repeated until the n-th unit zone corresponding to the unsteady zone is read out. If NO or j≠0, the process advances to Step S111. In Step S111, it is determined whether of a successive number j of 1st to j-th unsteady zones satisfying the condition I is equal to or greater than a given number jx (j≧jx) (wherein jx is a successive number which suggests a possibility of the REM sleep state). If NO or the successive number j is less than the given number jx, each of the successive number j of 1st to j-th unit zones described in Step S106 is discriminated as the light sleep zone. If YES or the successive number j is equal to or greater than the given number jx, the process advances to Step S112. In Step S112, each of the successive unit zones is discriminated as the (tentative) REM sleep zone, because the successive number J of 1st to j-th unit zones are highly likely to be in the REM sleep state.

If the successive unit zones include an apneic state due to sleep apnea syndrome or the like, a labored respiration will occur. Thus, the "respiratory rate of the target n-th unit zone" in the condition I in Step S105 will be increased. Thus, the condition I is determined based on such an abnormal value, and a zone to be discriminated as the light sleep zone is undesirably discriminated as the (tentative) REM sleep zone. For avoiding this risk, in Step S113, it is determined whether the steady state during sleep (i.e. deep sleep state or light sleep state) appears at a given ratio k or more, based on a condition K of "the number of steady zones in the entire in-bed zone/(the number of unit zones in the entire in-bed zone−the number of wake zones)≧k". That is, it is determined whether at least a sleep regarded as normal is maintained. Further, satisfaction of the condition K means that the sleep is normal and the determination result of the condition I is reasonable. Thus, If the determination in Step 113 is YES, in Step S115, each of the successive number J of 1st to j-th unit zones is discriminated as the REM sleep zone. If the determination in Step 113 is NO or the condition K is not satisfied, which means the presence of an abnormal sleep state, the process advances to Step 114 so as to perform an additional determination based on the following condition L.

The condition L is configured as follows: "(a maximum respiratory rate in each of the unit zones−a minimum respiratory rate in each of the unit zones)/the number of REM sleep zones≧Lx" in a successive number j of 1st to j-th (tentative) REM sleep zones, wherein Lx is a minimum value defining that a respiration is abnormal. The condition L is intended to adequately determine whether a respiratory rate is in a normal range even if the respiratory rate fluctuates. That is, the condition L is configured on the assumption that an apneic state occurs in one or more of the successive number j of 1st to j-th (tentative) REM sleep zones. Thus, if the determination in Step S114 is YES or the condition L is satisfied, which means the presence of abnormal respiration, each of the successive number j of 1st to j-th unit zones which have been discriminated as the (tentative) REM sleep zones is discriminated as the light sleep zone, in Step S106. If the determination is NO or the condition L is not satisfied, which means normality in respiration, each of the successive number j of 1st to j-th unit zones which have been discriminated as the (tentative) REM sleep zones is discriminated as the REM sleep zone, in Step S115.

In Step S107, the discriminated REM sleep zones and light sleep zones are stored on the storage section 9 in association with the corresponding unit zones. Then, in Step S108, the successive number j is initialized to zero. In Step S109, it is determined whether all of the 1-th to n-max-th unit zones have been subjected to this determination process. If NO or all of the unit zones have not been completely subjected to the determination process, the process will be repeated from Step S102. If YES or all of the unit zones have been subjected to the determination process, the process returns to the main routine illustrated in the flowchart of FIG. 4, and advances to the next determination subroutine.

Figure 16:
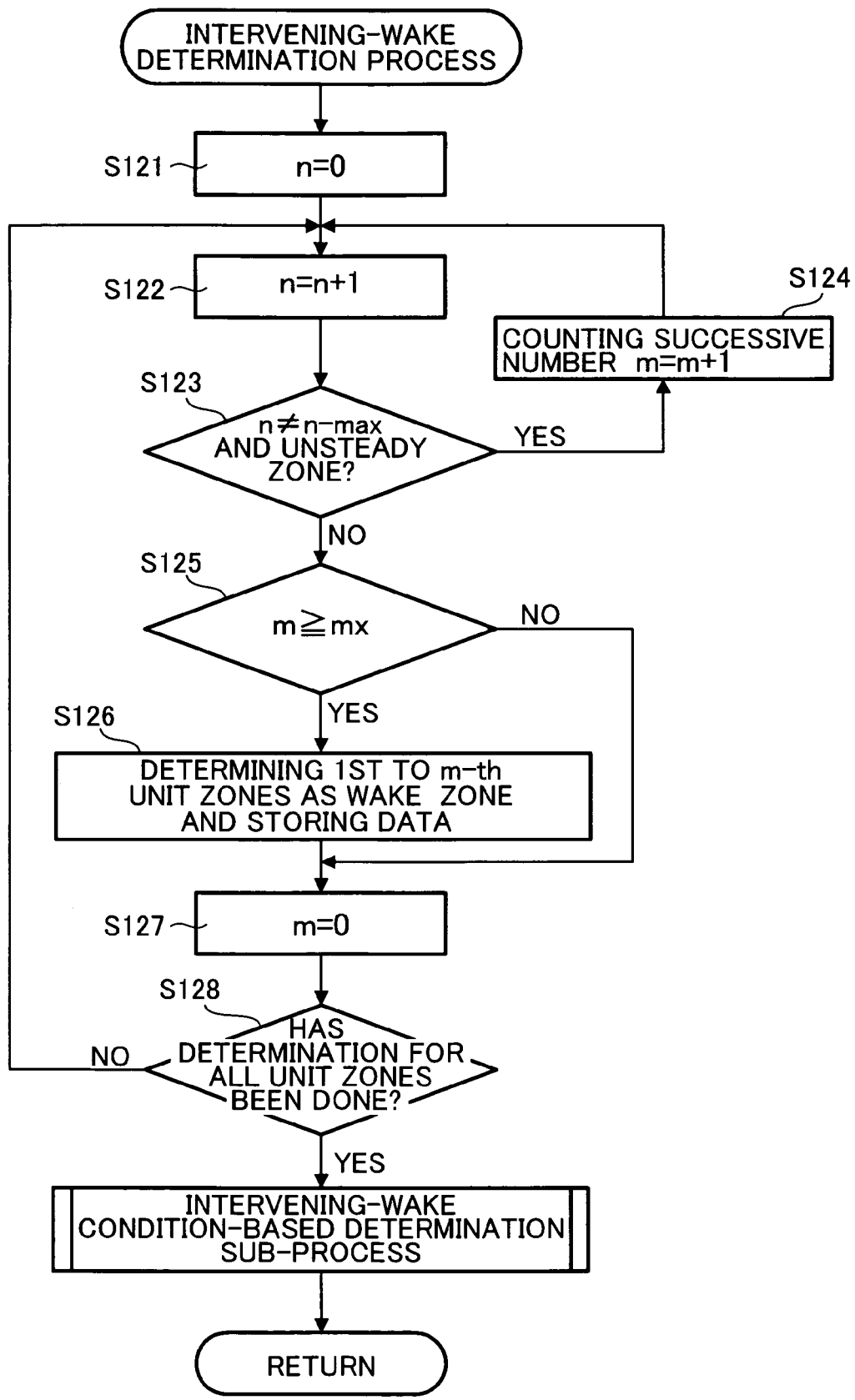
FIG. 16 is a flowchart showing a subroutine of an intervening-wake determination process.

With reference to the flowchart of FIG. 16, the intervening-wake determination subsection 17 will be described below.

When a body movement continues for a given time even in a sleep state, it can be regarded as wake during sleep (or intervening-wake). Thus, the following intervening-wake determination process will be performed.

In order to perform the intervening-wake determination process on an unit zone-by-unit zone basis as in the above processes, in Step S121, the "n" of the unit zone is initialized to zero (n=0). In Step S122, the "n" is set to n+1 (n=n+1), and respiratory data corresponding to this target n-th unit zone is read out. In Step S123, it is determined whether the read or target n-th unit zone is not the n-max-th unit zone (n≠n-max), and is either one (hereinafter referred to as "body movement zone") of the gross body movement zone and the fine body movement zone in the gross, fine and no body movements discriminated by the body-movement determination subsection 12 described in detail in connection with FIG. 7.

If the determination in Step S122 is YES or the target n-th unit zone is not the n-max-th unit zone (n≠n-max), and is the body movement zone, the process advances to Step S124. In Step S124, the successive number m is set to m+1 (m=m+1). Then, in Step S122, the "n" is set to n+1 again (n=n+1) to repeatedly detection the body movement zone. If the determination in Step S122 is NO or the target n-th unit zone is the n-max-th unit zone (n=n-max) or is the body movement zone, the process advances to Step S125. In Step S125, it is determined whether a successive number m satisfies the following relation: m≧mx (wherein mx is a successive number of the body movement zones which is indicative of a possibility of intervening-wake). If YES or m≧mx, the process advances to Step S126. In Step S126, each of the successive number m of 1st to m-th unit zones is discriminated as the wake state. Then, even if these unit zones are currently stored on the storage section 9 in such as manner as to be defined as the deep sleep zone, the light sleep zone or the REM sleep zone, each of the discriminated unit zones is redefined as the wake zone and stored on the storage section 9. Subsequently, in Step S127, the successive number m is initialized to zero.

Figure 17:
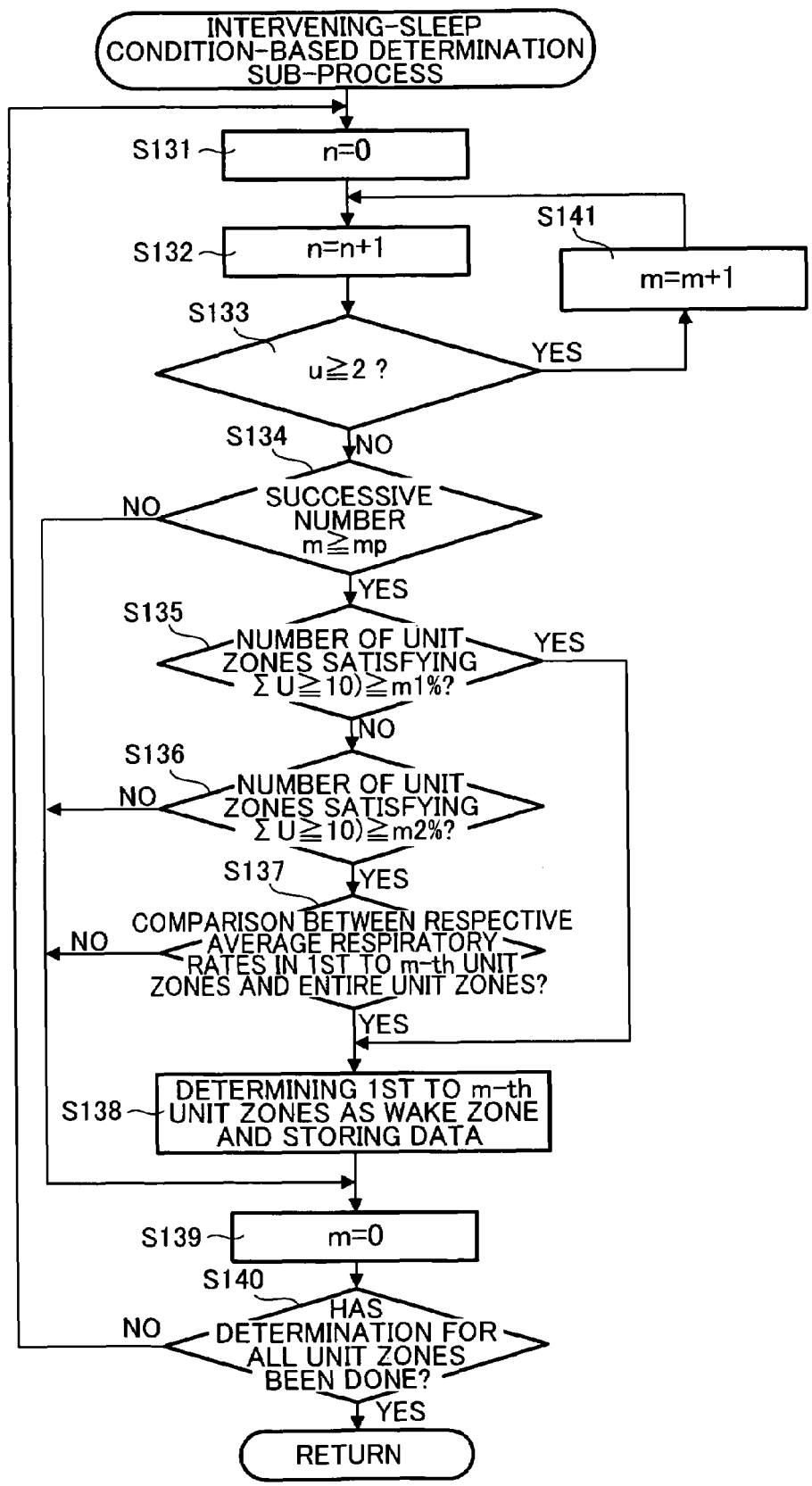
FIG. 17 is a flowchart showing a sub-subroutine of an intervening-wake condition determination process.

If the determination in Step S125 is NO or the successive number m is less than mx, the process skips from Step S125 to Step S127 so as to initialize the successive number m to zero (m=0). Then, in Step S128, it is determined whether all of the 1st to n-max-th unit zones have been subjected to the above process. If NO or all of the unit zones have not been completely subjected to the above process, the process will be repeated from Step S102. If YES or all of the unit zones have been subjected to the above process, the process advances to an intervening-wake condition-based determination sub-process as shown in FIG. 17, to specifically discriminate an intervening-wake using conditions defined based on a human intervening-wake pattern, which have been developed by the inventor through actual experimental tests. After completion of this determination sub-process, the process returns to the main routine illustrated in the flowchart of FIG. 4, and advances to the next determination process.

With reference to the flowchart of FIG. 17, the intervening-wake condition-based determination sub-process will be described below. In the intervening-wake condition-based determination sub-process, the "n" of the unit zone is initialized to zero (n=0) in Step S131, and the "n" is set to n+1 (n=n+1) to read respiratory data corresponding to this target n-th unit zone.

In Step S133, a body movement state in each of the unit zones is firstly discriminated. Specifically, as to the gross, fine and no body movement states discriminated and stored in association with one respiration i in Step S39 illustrated in the flowchart of FIG. 7 and described in connection with the body-movement determination subsection 12, "2", "1" and "0 (zero)" are assigned, respectively, to the gross movement state (U=2), the fine movement state (U=1) and the no body movement state (U=0), and the body movement state corresponding to each respiration i in the target n-th unit zone is expressed by a sum of the Us (hereinafter referred to as "ΣU").

Then, it is determined whether the target n-th unit zone satisfies the following relation: $\Sigma U \geq 2$. If YES or $\Sigma U \geq 2$, the process advances to Step S134. In Step S134, the successive number m is counted in a manner of m=m+1. If NO or $\Sigma U \geq 2$ is not satisfied, the process skips from Step S133 to Step 135 without counting a successive number. In Step S135, it is determined whether a previously counted successive number m satisfies the following relation: m≧mp (wherein mp is a constant which represents a successive number of body movement zones having a possibility of intervening-wake, and satisfies the following relation: mp<mx). If NO or m≧mp is not satisfied, which means no possibility of intervening-wake, the successive number m is initialized to zero (m=0) in Step S140. If YES or m≧mp is satisfied, which means a possibility that each of the successive number m of 1st to m-th unit zones is in the wake state, the following condition-based determination operation.

In Step S136, it is determined whether the following relation is satisfied in the successive number m of 1st to m-th unit zones: "(the number of unit zones each satisfying $\Sigma U \geq 10$)≧m1%" (wherein m1 is a constant which represents a ratio relative to the entire successive number m). If YES or this condition is satisfied, the process advances to Step S139. In Step S139, each of the successive number m of 1st to m-th unit zones is redefined as the wake zone, and then stored on the storage section 9. If NO or the above condition is not satisfied, the following condition-based determination operation is performed.

In Step S137, it is determined whether the following relation is satisfied: "(the number of unit zones each satisfying $\Sigma U \geq 10$)≧m2%" (wherein m2 is a constant which represents a ratio relative to the entire successive number m, and satisfied the following relation: m2<m1). If NO or this condition is not satisfied, which means no possibility of the presence of intervening-wake in the 1st to m-th unit zones, the succession number m is initialized to zero (m=0). If YES or the above condition is satisfied, which means a possibility of the presence of intervening-wake, the following condition is further added.

In Step S138, it is determined whether the following condition is satisfied: "(an average respiratory rate in the 1st to m-th unit zones)≧(an average respiratory rate in the 1st to n-max-th unit zones)×mq" (wherein mq is a constant satisfying the following relation: mq>1). Generally, a respiratory rate in the wake state is greater than that in the sleep state. Thus, if the average respiratory rate in the 1st to m-th unit zones including the sleep state is greater than "(the average respiratory rate in the 1st to n-max-th unit zones)×mq", this state can be clearly discriminated as the wake state.

If NO or the above condition is not satisfied, which means no possibility of the presence of intervening-wake in the 1st to m-th unit zones, the successive number m is initialized to zero in Step S140. If YES or the above condition is satisfied, the process advances to Step S139. In Step S139, each of the successive number m of 1st to m-th unit zones is redefined as the wake zone, and stored on the storage section 9. Then, in Step S140, the successive number m is initialized to zero. In Step S141, all of the 1st to n-max-th unit zones have been subjected to the above determination sub-process. If NO or all of the unit zones have not been completely subjected to the determination sub-process, the process will be repeated from Step S132. If YES or all of the unit zones have been subjected to the determination sub-process, the process returns to the subroutine illustrated in the flowchart of FIG. 1.

Figure 18:
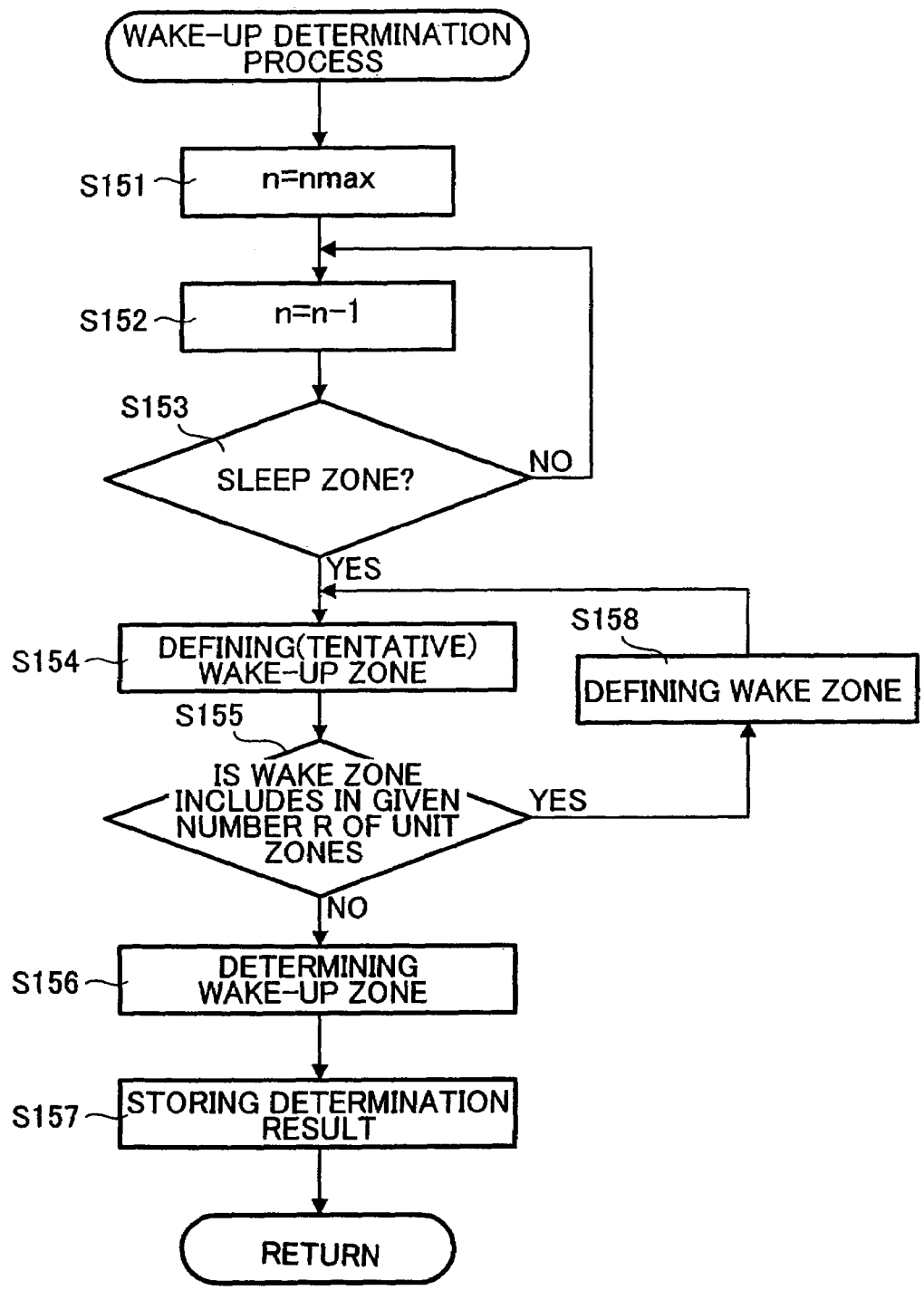
FIG. 18 is a flowchart showing a subroutine of a wake-up determination process.

With reference to the flowchart of FIG. 18, the operation of the wake-up determination subsection 18 will be described.

In Step S151, a target unit zone is first set at the n-max-th unit zone. Then, in Step S152, the "n" is set to n−1 (n=n−1) in a temporally retrograde direction, and a corresponding n-th unit zone is read out. In Step S153, it is determined whether the read n-th unit zone is defined as the sleep state, or either one (hereinafter referred to as sleep zone) of the deep sleep zone, the light sleep zone and the REM sleep zone. If NO or the n-th unit zone is not the sleep zone, the "n" is set to n+1 again in Step S152, and the operation for detecting the sleep zone will be repeated. If YES or the n-th unit zone is the sleep zone, this n-th unit zone is defined as a (tentative) wake-up zone. Then, in Step S155, it is determined whether a wake zone is included in a given number R of unit zones counted from the (tentative) wake-up zone in the temporally backward direction. Generally, it is considered that a wake state never occurs beyond a given time period before wake-up, during a human normal sleep. From this stand point, the given number R is set to define the given time period. If the determination in Step S155 is YES or the wake zone is included in the given number R of unit zones, the process advances to Step S158. In Step S158, each of the unit zones between the detected wake zone and the (tentative) wake-up zone is defined as the wake zone. Then, a unit zone next to and on the forward side of the detected wake zone is redefined as a new (tentative) wake-up zone, in Step S154, and the given number R of unit zones are rearranged, in Step S155.

If the above determination in Step S155 is NO or no wake zone is includes in the given number R of unit zones, the (tentative) wake-up zone is determined as a wake-up zone. Then, in Step S157, the determined wake-up zone is stored on the storage section 9 in association with a corresponding n-th unit zone. Then, the process retuned to the main routine illustrated in the flowchart of FIG. 4.

While the sleep stage determination apparatus 1 according to the above embodiment is designed to detect a respiratory signal using a mattress and a capacitor microphone, any other suitable conventional device capable of detecting a respiratory signal may be used. For example, a device adapted to be placed under a mattress so as to detect a pressure variation of the body of a human subject may include a piezoelectric element, such as piezoelectric cable, a capacitance-type sensor, a film sensor and a strain gauge. Further, a device for measuring a dynamic state of respiration using a resistance wire to be attached on an abdominal or chest region, or a device for directly measuring respiration using a mask for respiratory analysis.

Figure 13:
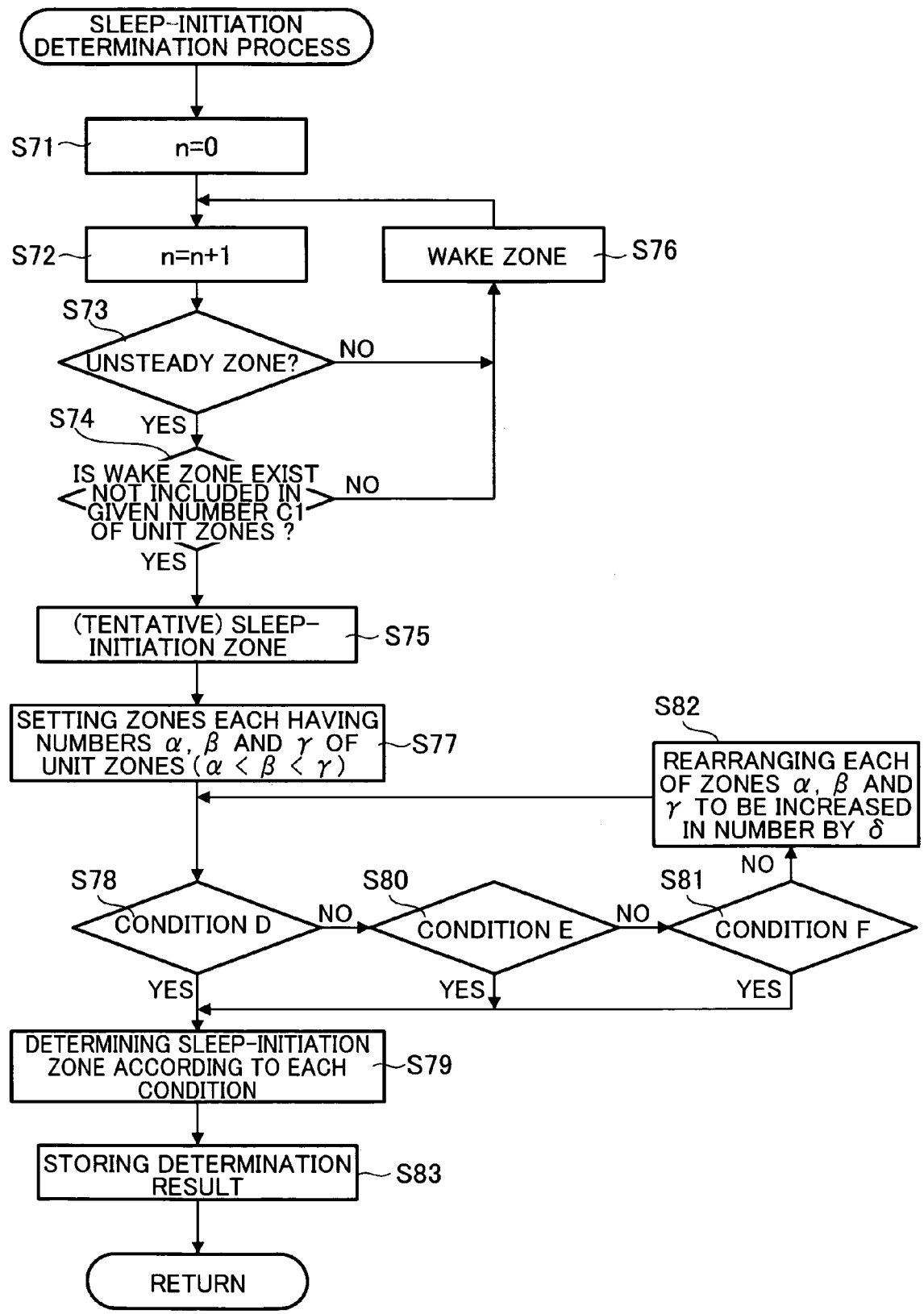
FIG. 13 is a flowchart showing a subroutine of a sleep-initiation determination process.

In Step 77 and subsequent Steps in the flowchart of FIG. 13 and for use in connection with the description about the sleep-initiation determination subsection 14, the determination process is performed based on the conditions D, E, F using a fluctuation $\sigma^2$, $\sigma \alpha^2$, $\sigma \beta^2$ and $\sigma \gamma^2$ in respiratory rate. Alternatively, a fluctuation in respiratory amplitude or a respiratory cycle may be used.

Further, in Step S138 for the intervening-wake condition-based determination sub-process described in connection with the flowchart of FIG. 17, the intervening-wake is discriminated based on respiratory rate using the condition of "(an average respiratory rate in the 1st to m-th unit zones)≧(an average respiratory rate in the 1st to n-max-th unit zones)× mq". In his case, heartbeat signal detection means for detecting a heartbeat-related parameter, and correction means for correcting the sleep stages using the detected heartbeat-related parameter may be combined therewith. For example, a condition of "(an average heart rate in the 1st to m-th unit zones)≧(an average heart rate in the 1st to n-max-th unit zones)×mv (wherein mv is a constant satisfying mv>1)" may be added to discriminate a wake state based on satisfaction of this condition so as to allow the wake state to be discriminates with a higher degree of accuracy.

Furthermore, a correlation between respective transition of a determination result from the sleep stage determination apparatus 1 and a parameter about hear rate detected by the heartbeat signal detection means may be appropriately adjusted to correct the determination result.

What is claimed is:

1. A sleep stage determination apparatus comprising:
   respiratory-signal detection means for detecting a variation in a respiratory signal from the body of a human subject; and
   sleep-stage determination means for determining a plurality of sleep stages with respect to each of a plurality of unit zones defined by segmenting said respiratory-signal variation on a given time period basis, said sleep-stage determination means including:
   in-bed/out-of-bed determination means for determining between an in-bed state and an out-of bed state, based on said respiratory-signal variation;
   body-movement determination means for determining the presence and level of a body movement, based on said respiratory-signal variation;
   wake determination means and intervening-wake determination means for determining between a wake state and a sleep state, based on a determination result of said body-movement determination means;
   sleep-initiation determination means for determining a sleep-initiation state having a transition from the wake state to the sleep state, based on said respiratory-signal variation, and the respective determination results of said in-bed/out-of-bed and wake determination means;
   sleep determination means for determining a depth of sleep based on said respiratory-signal variation, and respective determination results of said in-bed/out-of-bed, body-movement, sleep-initiation and wake determination means; and
   wake-up determination means for determining a wake-up state based on said respiratory-signal variation, and respective determination results of said in-bed/out-of-bed, body-movement, sleep-initiation, wake and sleep determination means;
   wherein said in-bed/out-of-bed determination means is operable, when said respiratory signal continues for a given time period or more at an amplitude equal to or greater than a given threshold value, to discriminate said in-bed state;
   wherein said body-movement determination means is operable to discriminate one of a gross body movement state, a fine body movement state and a no body movement state, based on a plurality of threshold values assigned, respectively, to an amplitude fluctuation and amplitude level of said respiratory signal and a cycle of said respiratory signal; and
   wherein said threshold value assigned to the amplitude fluctuation of said respiratory signal is compared to a standard deviation of amplitudes of three consecutive respiratory signals.

2. The sleep stage determination apparatus as defined in claim 1, wherein said wake determination means is operable to discriminate one of a wake state, an unsteady state and a steady state, based on a variation of the body movement state within a given time period.

3. The sleep stage determination apparatus as defined in claim 1, wherein said intervening-wake determination means is operable, when the body movement continues for a given time period or more at a given level or more, to discriminate said given time period of wake state.

4. The sleep stage determination apparatus as defined in claim 1, wherein said sleep-initiation determination means is operable to discriminate the wake state based on a transition pattern of an initial wake state and a variation pattern of the respiratory signal in a region around sleep initiation of the subject, to determine said sleep initiation state.

5. The sleep stage determination apparatus as defined in claim 1, wherein said sleep-initiation determination means includes deep-sleep determination means for determining a deep sleep state, and REM-sleep/light-sleep determination means for determining a REM-sleep state and a light-sleep state.

6. The sleep stage determination apparatus as defined in claim 5, wherein said deep-sleep determination means is operable, when each of a respiratory rate within a given time period, a fluctuation of the respiratory rate and a fluctuation of a respiratory cycle is equal to or less than a given threshold, and there is no body movement within a given time period, to discriminate said deep sleep state.

7. The sleep stage determination apparatus as defined in claim 5, wherein said REM-sleep/light-sleep determination means is operable to make a determination based on comparing between a respiratory rate within a given time period and an average respiratory rate of the entire sleep states and counting a successive number of said given time periods, and a determination based on whether an apneic state is present or absent within said given time period, so as to discriminate said REM-sleep state and said light-sleep state in accordance with said determination results.

8. The sleep stage determination apparatus as defined in claim 1, wherein said wake-up determination means is operable, when no wake state appears before a given time period elapses from a time of the last determination of the wake state, to discriminate that said wake-up state occurs at said time of the last determination of the wake state.

9. The sleep stage determination apparatus as defined in claim 1, which further includes:
   heartbeat signal detection means for detecting a heartbeat-related parameter; and
   correction means for correcting said sleep stages using said detected heartbeat-related parameter.

* * * * *

UNITED STATES PATENT AND TRADEMARK OFFICE
CERTIFICATE OF CORRECTION

| | |
|---|---|
| PATENT NO. | : 7,427,270 B2 |
| APPLICATION NO. | : 11/393668 |
| DATED | : September 23, 2008 |
| INVENTOR(S) | : Shuichi Izumi et al. |

Page 1 of 1

It is certified that error appears in the above-identified patent and that said Letters Patent is hereby corrected as shown below:

On the title page, below Item "(65)", insert the following:

--(30)    Foreign Application Priority Data
        April 1, 2005  (JP).......2005-105629--

Signed and Sealed this

Seventeenth Day of February, 2009

JOHN DOLL
*Acting Director of the United States Patent and Trademark Office*